United States Patent [19]

Guindon et al.

[11] Patent Number: 4,876,246

[45] Date of Patent: Oct. 24, 1989

[54] BENZO[A]PHENOTHIAZINES AND HYDRO-DERIVATIVES FOR INHIBITING LEUKOTRIENE BIOSYNTHESIS

[75] Inventors: Yvan Guindon, Closse Ile Bizard; Yves Girard; Cheuk K. Lau, both of Pierrefonds; Rejean Fortin, Montreal; Joshua Rokach, Laval; Christiane Yoakim, Montreal, all of Canada

[73] Assignee: Merck Frosst Canada, Inc., Kirkland, Canada

[21] Appl. No.: 183,944

[22] Filed: Apr. 20, 1988

Related U.S. Application Data

[60] Continuation of Ser. No. 871,342, Jun. 6, 1986, abandoned, which is a division of Ser. No. 716,878, Mar. 28, 1985, Pat. No. 4,611,056, which is a continuation-in-part of Ser. No. 654,994, Sep. 26, 1984, abandoned, which is a continuation-in-part of Ser. No. 539,215, Oct. 5, 1983, abandoned.

[51] Int. Cl.⁴ .................. A61K 31/54; A61K 31/535; A61K 31/675
[52] U.S. Cl. .................................. 514/80; 514/224.5; 514/229.5
[58] Field of Search ................ 514/80, 223, 233, 239, 514/240, 227

[56] References Cited

U.S. PATENT DOCUMENTS 3,580,947 5/1971 Ikeda et al. ................... 514/31 X

FOREIGN PATENT DOCUMENTS 681996 11/1968 South Africa .

OTHER PUBLICATIONS

J. Inst. Chem. (India) 49, 286–287, 1977 (Mital et al.).
J. Org. Chem. 32, 1193–1194, 1967 (Jackson et al.).
J. Org. Chem. 34, 1691–1694, 1969 (Van Allan et al.).
J. Med. Chem. 11, 622–623, 1968 (Jackson et al.).
Acta. Chim. Acad. Sci. Hung. 92, 89–97, 1977 (Agarwal et al.).
An. Org. Chem. 33B, 214–215, 1978 (Tiwari et al.).
Indian J. Chem. Sect. B, 17B, 408–409, 1979 (Tiwari et al.).
J. Het. Chem. 19, 167–169, 1982 (Ueno et al.).
Morrison et al., Org. Chem., 1966, Allyn & Bacon, Inc., Boston, pp. 96–101 & 282–290.

Primary Examiner—Leonard Schenkman
Attorney, Agent, or Firm—Gabriel Lopez; Hesna J. Pfeiffer

[57] ABSTRACT

Pharmaceutical compositions containing a compound of Formula I:

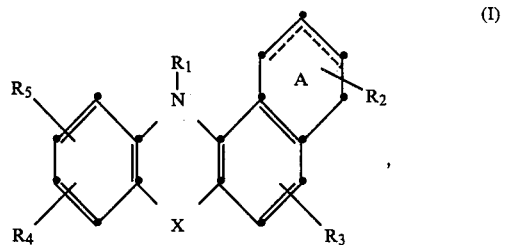

wherein X is O, S, SO or $SO_2$ and $R_2$, $R_3$, $R_4$ and $R_5$ may be positioned anywhere on the structure, or a pharmaceutically-acceptable salt thereof and certain novel benzo[a]phenothiazines, which compositions and compounds are useful in treating allergic conditions, asthma, cardiovascular disorders, inflammation and pain and are useful as cytoprotective agents.

14 Claims, No Drawings

BENZO[A]PHENOTHIAZINES AND HYDRO-DERIVATIVES FOR INHIBITING LEUKOTRIENE BIOSYNTHESIS

Continuation of U.S. Ser. No. 871,342, filed June 6, 1986, abandoned, which is a Division of U.S.S.N. 716,878, Mar. 28, 1985, now U.S. Pat. No. 4,611,056, which is a CIP of U.S. Ser. No. 654,994, Sept. 26, 1984, abandoned, which is a CIP of U.S. Ser. No. 539,215, Oct. 5, 1983, abandoned.

Benzo[a]phenothiazine and hydro-derivatives and analogs thereof are useful as inhibitors of the biosynthesis of mammalian leukotrienes. As such, these compounds are useful therapeutic agents for treating allergic conditions, asthma, cardiovascular disorders, inflammation and pain.

These compounds may be used to treat or prevent mammalian (especially human) disease states, such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents, such as $CCl_4$ and D-galactosamine; ischemic renal failure; disease-induced hepatic damage; bile salt induced pancreatic or gastric damage; trauma- or stress-induced cell damage; and glycerol-induced renal failure.

BACKGROUND OF THE INVENTION

The leukotrienes are a novel group of biologically-active substances derived from arachidonic acid through the action of the 5-lipoxygenase enzyme system. There are two groups of leukotrienes derived from a common unstable precursor Leukotriene $A_4$. The first of these are the peptido-lipid leukotrienes, the most important being Leukotrienes $C_4$ and $D_4$. These compounds collectively account for the biologically-active material known as the slow reacting substance of anaphylaxis.

The leukotrienes are potent smooth muscle-contracting agents, particularly on respiratory smooth muscle but also on other tissue (e.g., gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils. It also effects other cell types such as lymphocytes and, for example, may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil-dependent mechanism. See: D. M. Bailey and F. B. Casey, *Ann. Rpts. Med. Chem.* 17, 203 (1982).

Because the leukotrienes have been implicated in numerous disease states, the inhibition of leukotriene biosynthesis and/or antagonism of leukotriene action, will provide a therapeutic benefit to patients suffering from these disease states. These disease states include, but are not limited to: asthma; allergic conditions, such as allergic rhinitis; skin diseases, including psoriasis and atopic dermatitis; inflammation; gouty arthritis; gall bladder spasms; and cardiovascular disorders, such as angina.

Certain benzo[a]phenothiazine derivatives of general Formula A are known compounds:

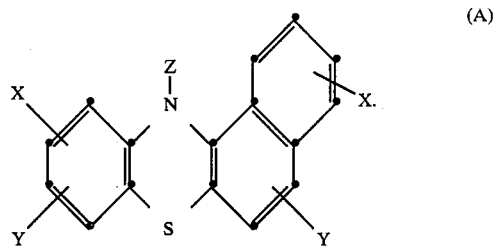

Some of these compounds have been used (inter alia) as antioxidants, dyes, whitening agents, photosensitizers and polymerization retardants. See for example; T. G. Jackson et al., *J. Org. Chem.* 32 1190–1194 (1967), J. A. Van Allen et al., *J. Organ. Chem.* 34 1691–1694 (1969), T. G. Jackson et al. *J. Med. Chem.* 11 622–623 (1968), N. L. Agarwal et al., *Acta Chim. Acad. Sci. Hung.* 92 89–97 (1977), R. L. Mital et al., *J. Inst. Chem. (India)* 49 286–287 (1977), J. P. Tiwari et al., *Anorg. Chem., Org. Chem.* 33B 214–215 (1978), J. P. Tiwari et al., *Indian J. Chem. Sect. B* 17B 408–409 (1979), Y. Ueno et al., *J. Heterocycl. Chem.* 19 167–169 (1982), S. Kikkawa et al., *Chemical Abstracts* 76 139757q (1972) and French Pat. No. 1,541,977 (1968).

It has been discovered that compounds of the Formula A type and analogs thereof are effective inhibitors of mammalian leukotriene biosynthesis and are thus useful in the treatment of leukotriene-mediated conditions, such as asthma, allergies, inflammation, and the like in mammals, especially in humans.

BRIEF DESCRIPTION OF THE DRAWINGS

FIG. 1 "Three dimensional" structure of 5-hydroxy-12-(1-acetoxyethoxycarbonyl)-12H-benzo[a]phenothiazine in crystalline form FIG. 2 Possible conformational isomers of 5-hydroxy-12-(1-acetoxyethoxycarbonyl)-12H-benzo[a]phenothiazine

DESCRIPTION OF THE INVENTION

The present invention relates to pharmaceutical compositions containing compounds of the Formula (I):

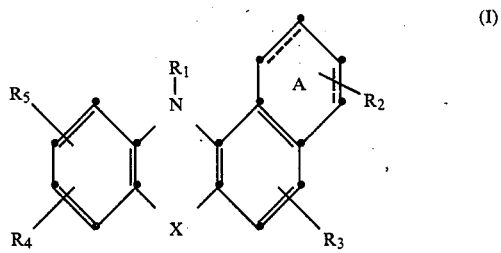

wherein X is O, S, SO or $SO_2$ and $R_2$, $R_3$, $R_4$ and $R_5$ may be positioned anywhere on the structure; pharmaceutically-acceptable salts thereof; a method of treatment using compounds of Formula I; and certain novel compounds of Formula I.

In one of its embodiments, the present invention relates to a pharmaceutical composition containing a compound of Formula I and a pharmaceutically-acceptable carrier:

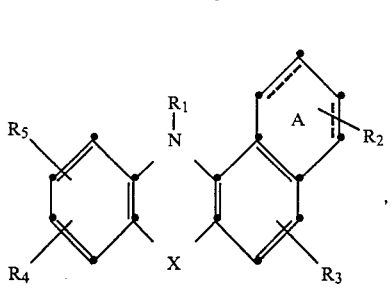

wherein:

X is O, S, SO or $SO_2$;

$R_1$ is H; $C_1$ to $C_6$-alkyl; $C_1$ to $C_6$-acyl; $C_1$ to $C_6$-aminoacyl; $C_1$ to $C_6$-acyloxy-$C_1$ to $C_6$-alkyl (e.g., —CH(CH_3)OCOC(CH_3)_3); $C_1$ to $C_6$-alkoxy-$C_1$ to $C_6$-alkyl (e.g., —CH(CH_3)C_2H_5);

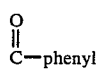

or

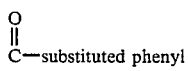

where the substituents of substituted phenyl are as defined below among the definitions of $R_{15}$; carbamoyl;

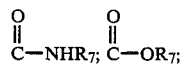

$SO_2$—$C_6H_4$—p—$CH_3$; $SO_2CH_3$; or $R_1$ is an acyl group, such that $R_1$—OH is an essential amino acid, where alkyl indicates straight- or branched-chain and cycloalkyl groups, acyl is defined as alkanoyl, and essential amino acids are the naturally-occurring amino acids, lysine, tryptophan, histidine, phenylalanine, leucine, isoleucine, threonine, methionine, valine, arginine, alanine, proline, glycine, serine, cysteine, tyrosine, asparagine, glutamine, aspartic acid and glutamic acid;

$R_2$, $R_3$, $R_4$ and $R_5$, all of which may be positioned anywhere on the structure, are independently selected from:

(1) hydrogen;
(2) alkyl having 1 to 6 carbon atoms;
(3) alkenyl having 2 to 6 carbon atoms;
(4) —(CH_2)_nM, where n is 0 to 6 and M is
   (a) $OR_{15}$;
   (b) halogen (F, Cl, Br or I);
   (c) $CF_3$;
   (d) $SR_{15}$, where $R_{15}$ is H; $C_1$ to $C_6$-alkoxy-$C_1$ to $C_6$-alkyl; $C_1$ to $C_6$-acyloxy-$C_1$ to $C_6$-alkyl; $C_1$ to $C_6$-alkyl; benzyl; —(CH_2)_nCOOR_6, wherein n is 0 to 6; CN; formyl; $C_1$ to $C_4$-perfluoroalkyl; $CH_2$-$R_{12}$, wherein $R_{12}$ is $C_1$ to $C_5$-alkyldimethylamino or phenyl; phenyl; substituted phenyl, wherein the substituents are $C_1$ to $C_3$-alkyl, halogen, CN, $CF_3$, $COOR_6$, $CH_2COOR_6$, $(CH_2)_pNR_8R_9$, where p is 0 to 2, $C_1$ to $C_3$-alkoxy or OH;
   (e) phenyl or substituted phenyl, wherein the substituents of substituted phenyl are as defined in $R_{15}$;
   (f) $COOR_6$;
   (g)

(h) tetrazole;
   (i)

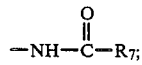

(j) —$NR_8R_9$;
   (k) —$NHSO_2R_{10}$ wherein $R_{10}$ is OH, $C_1$ to $C_6$-alkyl, $C_1$ to $C_6$-alkoxy, or phenyl;
   (l)

(m) —$SOR_{11}$, wherein $R_{11}$ is $C_1$ to $C_6$-alkyl; phenyl; substituted phenyl, where the substituents of substituted phenyl are as defined in $R_{15}$; $(CH_2)_mCOOR_6$, wherein m is 1 to 6; CN; formyl or perfluoro-$C_1$ to $C_4$-alkyl;
   (n) —$CONR_8R_9$;
   (o) —$SO_2NR_8R_9$;
   (p) —$SO_2R_{13}$, wherein $R_{13}$ is OH; $C_1$ to $C_6$-alkyl; H; phenyl; substituted phenyl where the substituents of substituted phenyl are as defined in $R_{15}$; $(CH_2)_mCOOR_6$, wherein m is 1 to 6; CN; formyl or perfluoro-$C_1$ to $C_4$-alkyl;
   (q) $NO_2$;
   (r)

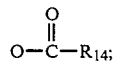

(s)

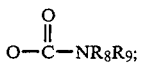

(t) —CN;
   (u) —$OPO(OR_6)_2$; or
   (v) $OR_a$, where $R_a$ is H; $C_1$ to $C_5$-alkyl; $C_1$ to $C_5$-acyl; $C_1$ to $C_6$-alkoxy-$C_1$ to $C_6$-alkyl; $C_1$ to $C_6$-acyloxy-$C_1$ to $C_6$-alkyl; $C_1$ to $C_4$-aminoacyl; carbamoyl;

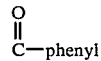

or

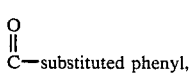

wherein the substituents on substituted phenyl are as defined in $R_{15}$;

where $R_c$ is $C_1$ to $C_4$-alkyl;

where $R_d$ is $C_1$ to $C_6$-alkyl or $C_1$ to $C_6$-acyloxy-$C_1$ to $C_4$-alkyl (e.g., $CH(CH_3)OCOCH_3$); or is a structure such that $-OR_a$ is an ester of an essential amino acid, wherein essential amino acids are as defined above; and (5) $-(CHR_6)_qCOOR_6$, where q is 0 to 4; where each $R_6$ is independently H, phenyl or $C_1$ to $C_6$-alkyl; each $R_7$ is $C_1$ to $C_6$-alkyl, benzyl, phenyl or $C_1$ to $C_6$-acyloxy-$C_1$ to $C_6$-alkyl; each $R_8$ and each $R_9$ is independently H, phenyl or substituted phenyl, where the substituents of substituted phenyl are as defined in $R_{15}$, or $C_1$ to $C_4$-alkyl, or an $R_8$ and an $R_9$ may be joined through the N to form a heterocycloalkyl of 5 to 8 ring atoms; each $R_{14}$ is independently H, OH, $(CH_2)_qCOOR_6$ where q is 0 to 4, $C_1$ to $C_6$-alkyl, $C_1$ to $C_6$-alkoxy, $C_1$ to $C_6$-acyloxy-$C_1$ to $C_6$-alkoxy, phenyl or substituted phenyl wherein the substituents of substituted phenyl are as defined in $R_{15}$, $C_1$ to $C_6$-aminoalkyl, or $R_{14}$ is such that $R_{14}CO_2H$ is an essential amino acid, as defined above; and the broken lines ($|\mathbin{|}$) in ring A represent single or double bonds.

Pharmaceutically-acceptable salts of the compounds described herein are also included within the scope of the present invention. Such salts may be prepared from pharmaceutically-acceptable non-toxic bases, including inorganic bases and organic bases when the compound is acidic. Salts derived from inorganic bases include sodium, potassium, lithium, ammonium, calcium, magnesium, ferrous, zinc, copper, maganous, aluminum, ferric, maganic salts and the like. Particularly preferred are the potassium, sodium, calcium, and magnesium salts. Salts derived from pharmaceutically-acceptable organic non-toxic bases include salts of primary, secondary, and teriary amines, substituted amines, including naturally-occurring substituted amines, cyclic amines and basic ion exchange resins, such as isopropylamine, tri-methylamine, diethanolamine, diethylamine, triethylamine, tripropylamine ethanolamine, 2-dimethylaminoethanol, 2-diethylaminoethanol, tomethamine, lysine, arginine, histidine, betaine, ethylenediamine, glucosamine, methylglucamine, theobromine, purines, piperazine, N,N'-dibenzylethylenediamine, piperidine, N-ethyl-piperidine, morpholine, N-ethylmorpholine, polyamine resins and the like.

When the compound is basic, salts may be prepared from pharmaceutically-acceptable non-toxic acids, including inorganic and organic acids. Such acids include hydrochloric, hydrobromic, sulfuric, nitric, isethionic, methanesulfonic, ethanesulfonic, benzenesulfonic, p-toluenesulfonic, acetic, benzoic, camphorsulfonic, citric, fumaric, gluconic, glutamic, lactic, malic, maleic, mandelic, mucic, pamoic, pantothenic, phosphoric, succinic; tartaric acid and the like. Particularly preferred are hydrochloric, hydrobromic, citric, maleic, phosphoric, sulfuric and tartaric acids.

For helpful discussion of pharmaceutical salts see S. M. Berge et al., Journal of Pharmaceutical Sciences, 66, 1-19 (1977), the disclosure of which is hereby incorporated herein by reference.

A preferred composition is comprised of compounds having the Formula II;

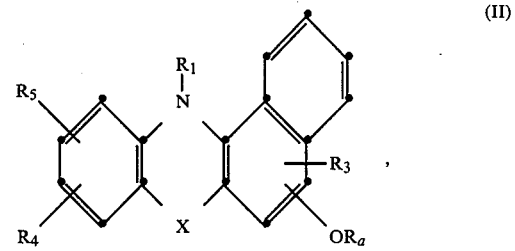

wherein:

$R_1$ is hydrogen, $C_1$ to $C_4$-alkyl, $C_1$ to $C_4$-acyl, $C_1$ to $C_6$-aminoacyl, $C_1$ to $C_6$-acyloxy-$C_1$ to $C_6$-alkyl (e.g., $CH(CH_3)OCOC(CH_3)_3$), or $-COOR_d$;

$R_3$, $R_4$ and $R_5$, all of which may be positioned anywhere on the structure, are each independently selected from hydrogen, halogen, $CH_3$, $CF_3$, $COCH_3$, $R_b$, $SR_6$, $CH_2OH$, $OR_b$, $COOR_b$ and $CH_2COOR_b$, where each $R_b$ is independently selected from H and $C_1$ to $C_4$-alkyl;

X, $R_a$, $R_d$, $R_6$, alkyl, acyl and halogen are as defined above, and $OR_a$ may be positioned anywhere on the structure.

A more preferred composition is comprised of compounds of Formula III:

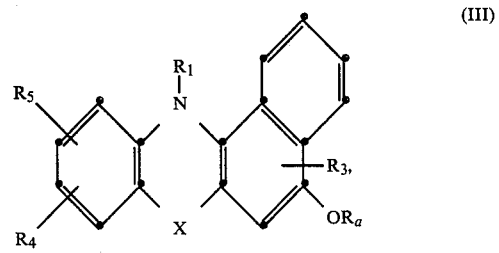

wherein:

X is O or S; and $R_1$, $R_3$, $R_4$, $R_5$ (where $R_3$, $R_4$ and $R_5$ may be positioned anywhere on the structure) and $R_a$ are as defined for Formula II compounds above.

A still more preferred composition is comprised of compounds of Formula III, wherein X is S and the remaining substituents are as defined for Formula III, with the proviso that at least one of $R_1$ or $R_a$ is not hydrogen.

Another preferred embodiment of the present invention comprises the novel compounds of Formula IIIa:

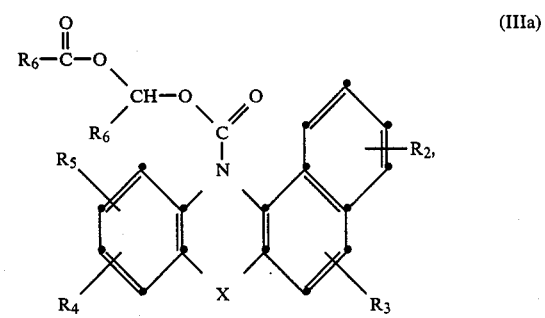

wherein X, $R_2$, $R_3$, $R_4$, $R_5$ (where $R_2$, $R_3$, $R_4$ and $R_5$ may be positioned anywhere on the structure) and $R_6$ are as defined for Formula I.

A particularly preferred series of novel compounds of Formula IIIa are those wherein:

X is S;
$R_2$ is OH and is located at position 5;
$R_6$ is $CH_3$; and
$R_3$, $R_4$ and $R_5$ are as defined for Formula I and may be placed anywhere on the structure.

Examples of the Formula I compounds useful in the compositions of the present invention are tabulated below in Table I (the number preceding the $R_2$-$R_5$ definitions signifying tha group's position on the ring system).

TABLE I
COMPOUNDS OF FORMULA I

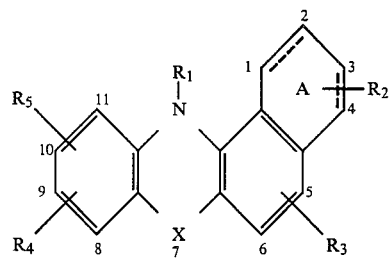
(I)

| Compound[a] | X | Ring A | $R_1$ | $R_2$ | $R_3$ | $R_4$ | $R_5$ |
|---|---|---|---|---|---|---|---|
| 1.[1] | S | aromatic | H | 5-OH | H | H | H |
| 2.[1] | S | aromatic | H | 5-OCOCH$_3$ | 6-Cl | H | H |
| 3. | S | aromatic | H | H | H | H | H |
| 4. | S | aromatic | H | 5-OH | 6-Cl | H | H |
| 5. | S | aromatic | H | 5-OH | 6-Cl | 9-Cl | H |
| 6. | S | aromatic | H | 5-OH | 6-Cl | 9-OCH$_3$ | H |
| 7. | S | aromatic | H | 5-OCOCH$_3$ | 6-Cl | 9-CH$_3$ | H |
| 8.[1] | O | aromatic | H | 5-OH | H | H | H |
| 9.[1,2] | O | aromatic | H | 5-OCOCH$_3$ | H | H | H |
| 10. | SO | aromatic | H | 5-OH | H | H | H |
| 11.[1,2] | SO$_2$ | aromatic | H | 5-OH | H | H | H |
| 12. | SO | aromatic | H | H | H | H | H |
| 13. | SO$_2$ | aromatic | H | H | H | H | H |
| 14. | SO | aromatic | COCH$_3$ | H | H | H | H |
| 15. | S | aromatic | H | 1-CO$_2$H | H | H | H |
| 16. | S | aromatic | CH$_3$ | 2-Et | H | H | H |
| 17. | S | aromatic | COCH$_3$ | 2-COCH$_3$ | H | H | H |
| 18. | S | aromatic | H | 2-COCH$_3$ | H | H | H |
| 19. | S | aromatic | H | H | H | H | 10-phenyl |
| 20. | S | aromatic | H | H | H | 8-CH$_3$ | 11-CH$_3$ |
| 21. | S | aromatic | H | H | H | H | 10-COCH$_3$ |
| 22. | S | aromatic | H | 5-OH | 6-NHCOCH$_3$ | 9-F | H |
| 23. | S | aromatic | H | 5-OH | 6-NH—phenyl | 9-Cl | H |
| 24. | SO | aromatic | H | 5-OAc | 6-Cl | H | 10-CF$_3$ |
| 25. | SO | aromatic | H | 5-OCH$_2$Ph | 6-Cl | H | 10-CF$_3$ |
| 26. | S | aromatic | H | 5-OH | 6-Cl | 9-CH$_3$ | 11-CH$_3$ |
| 27. | S | aromatic | H | 5-OCH$_3$ | 6-Cl | 9-OCH$_3$ | H |
| 28. | SO$_2$ | 1,4-dihydro | H | 5-OH | H | H | H |
| 29. | SO$_2$ | aromatic | COCH$_3$ | 4-CH$_3$ | H | 9-SCH$_3$ | H |
| 30. | O | aromatic | H | H | H | 9-SO$_2$CF$_3$ | H |
| 31. | O | aromatic | H | H | H | 11-CH$_3$ | H |
| 32. | S | aromatic | COCH$_3$ | 5-OCOMe | H | H | H |
| 33. | S | aromatic | CH$_2$OAc | 5-OH | H | H | H |
| 34. | S | aromatic | CH$_2$OAc | 5-OCOMe | H | H | H |
| 35.[1] | S | aromatic | Me | 5-OH | H | H | H |
| 36.[1,2] | S | aromatic | H | 5-OCOCH$_3$ | H | H | H |
| 37. | S | aromatic | CH$_3$ | 5-OCH$_3$ | H | H | H |
| 38. | S | aromatic | CH$_3$ | 5-OCOCH$_3$ | H | H | H |
| 39. | S | aromatic | COCH$_3$ | 5-OH | H | H | H |
| 40. | S | aromatic | COCH$_3$ | 5-OCH$_3$ | H | H | H |
| 41.[1] | S | aromatic | H | 5-OCOCH$_2$NH$_2$ | H | H | H |
| 42.[1] | S | 1,4-dihydro | H | 5-OH | H | H | H |
| 43.[1] | S | aromatic | H | 5-OCOCH(CH$_3$)$_2$ | H | H | H |
| 44.[1] | S | aromatic | H | 5-OCOC(CH$_3$)$_3$ | H | H | H |
| 45.[1] | S | aromatic | H | 5-OCOC$_6$H$_5$ | H | H | H |
| 46.[1] | S | aromatic | H | 5-OH | 6-CH$_3$ | H | H |
| 47.[1] | S | aromatic | H | 5-OCOCH$_3$ | 6-CH$_3$ | H | H |
| 48. | S | aromatic | H | 5-OH | 1-OH | 6-CH$_3$ | H |
| 49. | S | aromatic | H | 5-OCOCH$_3$ | 1-OH | 6-CH$_3$ | H |
| 50. | S | aromatic | H | 5-OH | 1-OCH$_3$ | 6-CH$_3$ | H |
| 51. | S | aromatic | H | 5-OCOCH$_3$ | 1-OCH$_3$ | 6-CH$_3$ | H |
| 52. | S | aromatic | H | 5-OCOC(CH$_3$)$_3$ | 1-OCH$_3$ | 6-CH$_3$ | H |
| 53. | S | 1,4-dihydro | H | 5-OCOCH$_3$ | H | H | H |
| 54. | SO$_2$ | 1,4-dihydro | H | 5-OCOCH$_3$ | H | H | H |
| 55. | SO | aromatic | H | 5-OCOCH$_3$ | H | H | H |

TABLE I-continued

COMPOUNDS OF FORMULA I

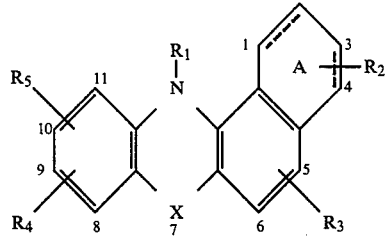
(I)

| Compound[a] | X | Ring A | R1 | R2 | R3 | R4 | R5 |
|---|---|---|---|---|---|---|---|
| 56.[1,2] | SO2 | aromatic | H | 5-OCOCH3 | H | H | H |
| 57. | S | aromatic | H | 5-OCH2OCH3 | H | H | H |
| 58. | S | aromatic | H | 5-OCH3 | H | H | H |
| 59. | S | aromatic | H | 5-OCOC6H4—p-OMe | H | H | H |
| 60. | S | aromatic | H | 5-OCOC6H4—p-Cl | H | H | H |
| 61. | S | aromatic | H | 5-OCOC6H4—p-NH2 | H | H | H |
| 62. | S | aromatic | H | 5-OCOC6H4—p-CO2H | H | H | H |
| 63. | S | aromatic | H | 5-OCOC6H4—O—CF3 | H | H | H |
| 64. | S | aromatic | H | 5-OCOC6H4—m-CN | H | H | H |
| 65. | S | aromatic | H | 5-OCO(CH2)2CO2H | H | H | H |
| 66. | S | aromatic | H | 5-OCO(CH2)4CO2H | H | H | H |
| 67. | S | aromatic | H | 5-OCOCH(NH2)CH3 | H | H | H |
| 68. | S | aromatic | H | 5-OCOCH(NH2)CH2C6H5 | H | H | H |
| 69.[1,2] | S | aromatic | CO2CHCH3<br>\|<br>OAc | 5-OH | H | H | H |
| 70.[1,2] | S | aromatic | CO2CHCH3<br>\|<br>OAc | 5-OAc | H | H | H |
| 71. | S | aromatic | CO2CHCH3<br>\|<br>OAc | 5-OCO2CHCH3<br>\|<br>OAc | H | H | H |
| 72 | S | aromatic | H | 5-OCO2CHCH3<br>\|<br>OAc | H | H | H |
| 73. | S | aromatic | H | 5-OPO(OEt)2 | H | H | H |
| 74. | S | aromatic | H | 5-OH | 9-OMe | H | H |
| 75. | S | aromatic | H | 5-OAc | 9-OMe | H | H |
| 76.[1] | S | aromatic | H | 5-OH | 9-Me | H | H |
| 77.[1] | S | aromatic | H | 5-OAc | 9-Me | H | H |
| 78. | S | aromatic | H | 5-OH | 9-F | H | H |
| 79. | S | aromatic | H | 5-OAc | 9-F | H | H |
| 80. | S | aromatic | H | 5-OH | 6-OAc | H | H |
| 81. | S | aromatic | H | 5-OAc | 6-OAc | H | H |
| 82. | S | aromatic | Ac | 5-OH | 6-OH | H | H |
| 83. | S | aromatic | Ac | 5-OAc | 6-OAc | H | H |
| 84. | SO2 | aromatic | H | 5-OH | 5-OH | H | H |
| 85.[1,2] | O | aromatic | OAc<br>\|<br>CO2CHCH3 | 5-OH | H | H | H |
| 86. | SO2 | aromatic | OAc<br>\|<br>CO2CHCH3 | 5-OH | H | H | H |
| 87.[1,2] | S | aromatic | OCOC(CH3)3<br>\|<br>CO2CHCH3 | 5-OH | H | H | H |
| 88.[1] | S | aromatic | CO2C2H5 | 5-OH | H | H | H |
| 89.[1] | S | aromatic | CO2CH(CH3)2 | 5-OH | H | H | H |
| 90.[1,2] | S | aromatic | OAc<br>\|<br>CHCH3 | 5-OH | H | H | H |
| 91.[1,2] | S | aromatic | OCOC(CH3)3<br>\|<br>CHCH3 | 5-OH | H | H | H |

TABLE I-continued
COMPOUNDS OF FORMULA I

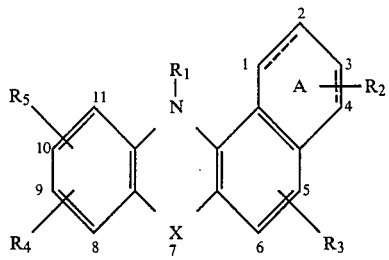

(I)

| Compound[a] | X | Ring A | $R_1$ | $R_2$ | $R_3$ | $R_4$ | $R_5$ |
|---|---|---|---|---|---|---|---|
| 92.[1,2] | S | aromatic | OAc\|CO$_2$CHCH$_3$ | 5-OH | 6-Cl | H | H |
| 93.[1,2] | S | aromatic | OAc\|CO$_2$CHCH$_3$ | 5-OH | 6-CF$_3$ | H | H |
| 94.[1,2] | S | aromatic | OAc\|CO$_2$CHCH$_3$ | 5-OH | 6-F | H | H | wherein Ac is acetyl, Et is ethyl, Me is methyl and Ph is phenyl.
[a]The symbol 1 next to the number of a compound indicates which compounds are preferred and the symbol 2 next to the number of a compound indicates which compounds are also more preferred.

Another embodiment of the present invention is novel compounds and their pharmaceutically-acceptable salts, encompassed by Formula I, examples of which are listed in Table II. The number preceding the $R_2$–$R_5$ definitions signifies that group's position on the ring system.

TABLE II
NOVEL COMPOUNDS OF FORMULA I

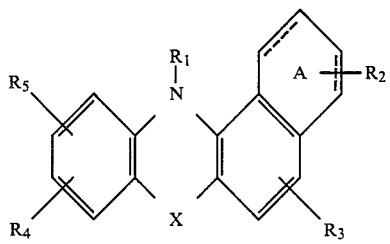

(I)

| Compound[a] | X | Ring A | $R_1$ | $R_2$ | $R_3$ | $R_4$ | $R_5$ |
|---|---|---|---|---|---|---|---|
| 1.[1] | S | aromatic | H | 5-OCOCH$_3$ | H | H | H |
| 2. | S | aromatic | CH$_3$ | 5-OCH$_3$ | H | H | H |
| 3. | S | aromatic | CH$_3$ | 5-OCOCH$_3$ | H | H | H |
| 4. | S | aromatic | COCH$_3$ | 5-OH | H | H | H |
| 5. | S | aromatic | COCH$_3$ | 5-OCH$_3$ | H | H | H |
| 6. | S | aromatic | H | 5-OCOCH$_2$NH$_2$ | H | H | H |
| 7. | S | 1,4-dihydro | H | 5-OH | H | H | H |
| 8. | S | aromatic | H | 5-OCOCH(CH$_3$)$_2$ | H | H | H |
| 9. | S | aromatic | H | 5-OCOC(CH$_3$)$_3$ | H | H | H |
| 10. | S | aromatic | H | 5-OCOC$_6$H$_5$ | H | H | H |
| 11. | S | aromatic | H | 5-OH | 6-CH$_3$ | H | H |
| 12. | S | aromatic | H | 5-OCOCH$_3$ | 6-CH$_3$ | H | H |
| 13. | S | aromatic | H | 5-OH | 1-OH | 6-CH$_3$ | H |
| 14. | S | aromatic | H | 5-OCOCH$_3$ | 1-OH | 6-CH$_3$ | H |
| 15. | S | aromatic | H | 5-OH | 1-OCH$_3$ | 6-CH$_3$ | H |
| 16. | S | aromatic | H | 5-OCOCH$_3$ | 1-OCH$_3$ | 6-CH$_3$ | H |
| 17. | S | aromatic | H | 5-OCOC(CH$_3$)$_3$ | 1-OCH$_3$ | 6-CH$_3$ | H |
| 18. | S | 1,4-dihydro | H | 5-OCOCH$_3$ | H | H | H |
| 19. | SO | aromatic | H | 5-OCOCH$_3$ | H | H | H |
| 20.[1] | SO$_2$ | aromatic | H | 5-OCOCH$_3$ | H | H | H |
| 21. | SO | aromatic | H | 5-OH | H | H | H |
| 22.[1] | SO$_2$ | aromatic | H | 5-OH | H | H | H |
| 23. | S | aromatic | H | 5-OCH$_2$OCH$_3$ | H | H | H |
| 24. | S | aromatic | H | 5-OCH$_3$ | H | H | H |
| 25. | S | aromatic | COCH$_3$ | 5-OCOCH$_3$ | H | H | H |
| 26. | S | aromatic | CH$_3$ | 5-OH | H | H | H |

TABLE II-continued
NOVEL COMPOUNDS OF FORMULA I

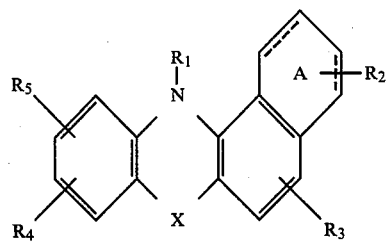

(I)

| Compound[a] | X | Ring A | $R_1$ | $R_2$ | $R_3$ | $R_4$ | $R_5$ |
|---|---|---|---|---|---|---|---|
| 27.[1] | S | aromatic | CO₂CHCH₃ \| OAc | 5-OH | H | H | H |
| 28.[1] | S | aromatic | CO₂CHCH₃ \| OAc | 5-OAc | H | H | H |
| 29. | S | aromatic | CO₂CHCH₃ \| OAc | 5-OCO₂CHCH₃ \| OAc | H | H | H |
| 30. | S | aromatic | H | 5-OCO₂CHCH₃ \| OAc | H | H | H |
| 31. | S | aromatic | H | 5-OPO(OEt)₂ | H | H | H |
| 32. | S | aromatic | H | 5-OH | 9-OMe | H | H |
| 33. | S | aromatic | H | 5-OAc | 9-OMe | H | H |
| 34. | S | aromatic | H | 5-OH | 9-Me | H | H |
| 35. | S | aromatic | H | 5-OAc | 9-Me | H | H |
| 36. | S | aromatic | H | 5-OH | 9-F | H | H |
| 37. | S | aromatic | H | 5-OAc | 9-F | H | H |
| 38. | S | aromatic | H | 5-OH | 6-OAc | H | H |
| 39. | S | aromatic | H | 5-OAc | 6-OAc | H | H |
| 40. | S | aromatic | Ac | 5-OH | 6-OH | H | H |
| 41. | S | aromatic | Ac | 5-OAc | 6-OAc | H | H |
| 42. | SO₂ | aromatic | H | 5-OH | 6-OH | H | H |
| 43. | O | aromatic | H | 5-OH | H | H | H |
| 44.[1] | O | aromatic | H | 5-OAc | H | H | H |
| 45.[1] | O | aromatic | OAc \| CO₂CHCH₃ | 5-OH | H | H | H |
| 46. | SO₂ | aromatic | OAc \| CO₂CHCH₃ | 5-OH | H | H | H |
| 47. | S | aromatic | H | 5-OH | 9-OCH₂CO₂H | H | H |
| 48. | S | aromatic | H | 5-OH | 6-Br | 9-CH₂CO₂H | H |
| 49.[1] | O | aromatic | OAc \| CO₂CHCH₃ | 5-OH | H | H | H |
| 50.[1] | S | aromatic | OCOC(CH₃)₃ \| CO₂CHCH₃ | 5-OH | H | H | H |
| 51. | S | aromatic | CO₂C₂H₅ | 5-OH | H | H | H |
| 52. | S | aromatic | CO₂CH(CH₃)₂ | 5-OH | H | H | H |
| 53.[1] | S | aromatic | OAc \| CHCH₃ | 5-OH | H | H | H |
| 54.[1] | S | aromatic | OCOC(CH₃)₃ \| CHCH₃ | 5-CH | H | H | H |
| 55.[1] | S | aromatic | OAc \| CO₂CHCH₃ | 5-OH | 6-Cl | H | H |
| 56.[1] | S | aromatic | OAc \| CO₂CHCH₃ | 5-OH | 6-CF₃ | H | H |

TABLE II-continued
NOVEL COMPOUNDS OF FORMULA I
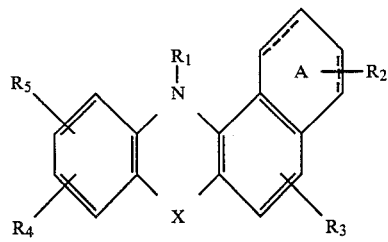
(I)
| Compound[a] | X | Ring A | R1 | R2 | R3 | R4 | R5 |
|---|---|---|---|---|---|---|---|
| 57.[1] | S | aromatic | OAc<br>\|<br>CO2CHCH3 | 5-OH | 6-F | H | H |
[a]The symbol 1 next to the number of a compound indicates which compounds are preferred.
The compounds of Formula I may be prepared by any process available to the skilled artisan.
Several such processes are illustrated in Schemes I to IV below.
SCHEME I
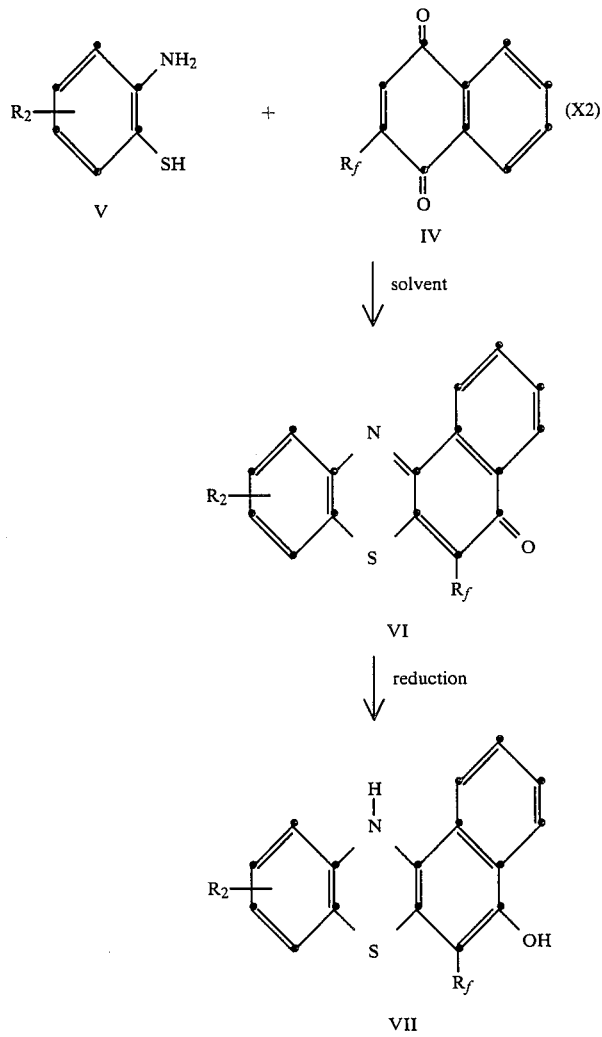

-continued
SCHEME I
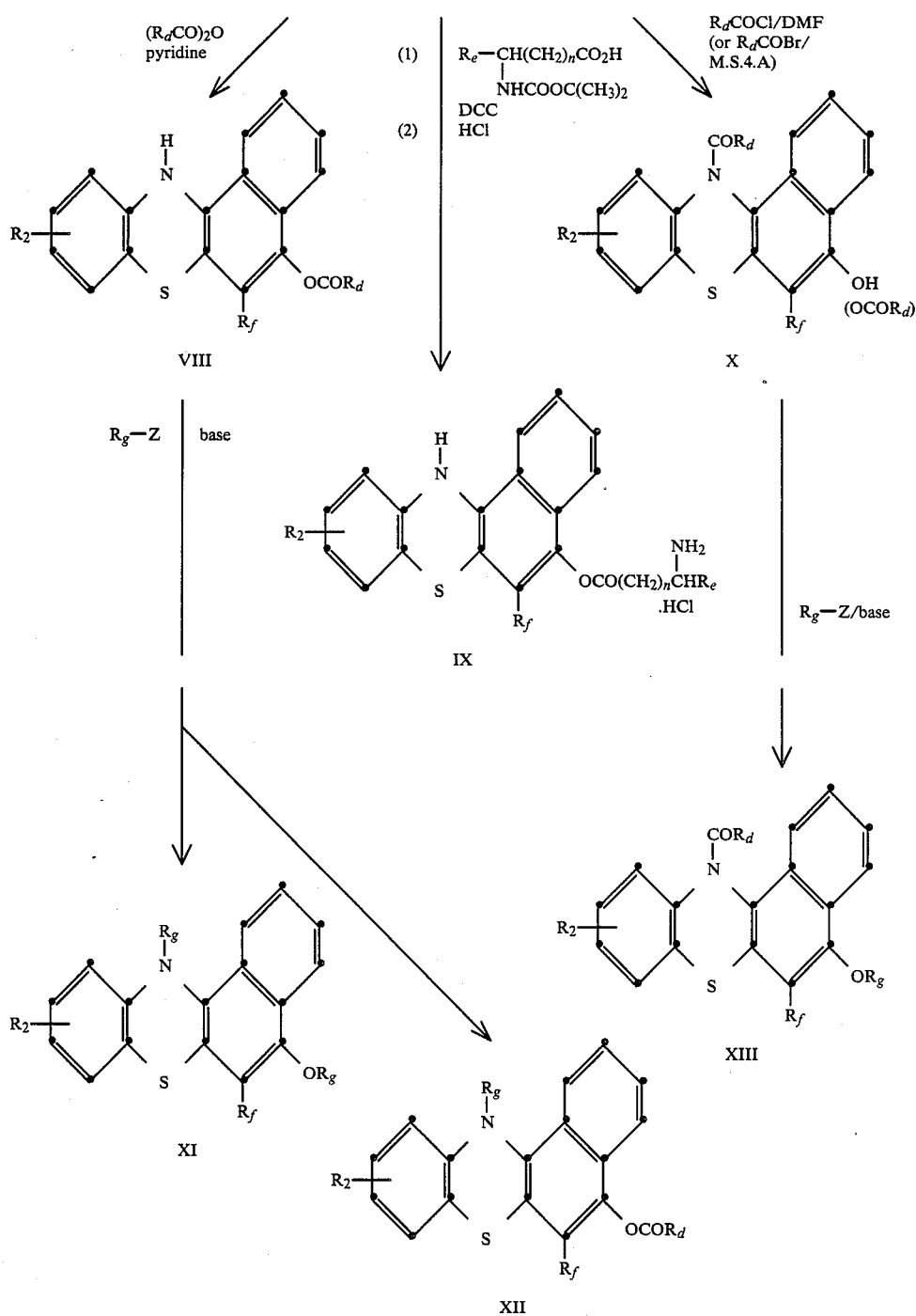

SCHEME II

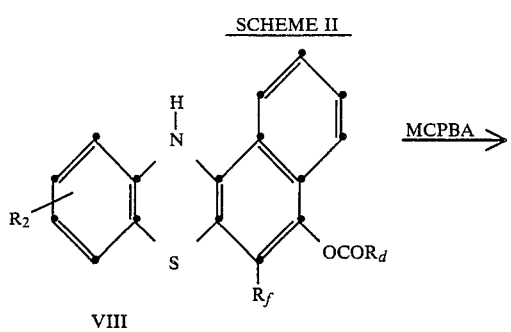

SCHEME III

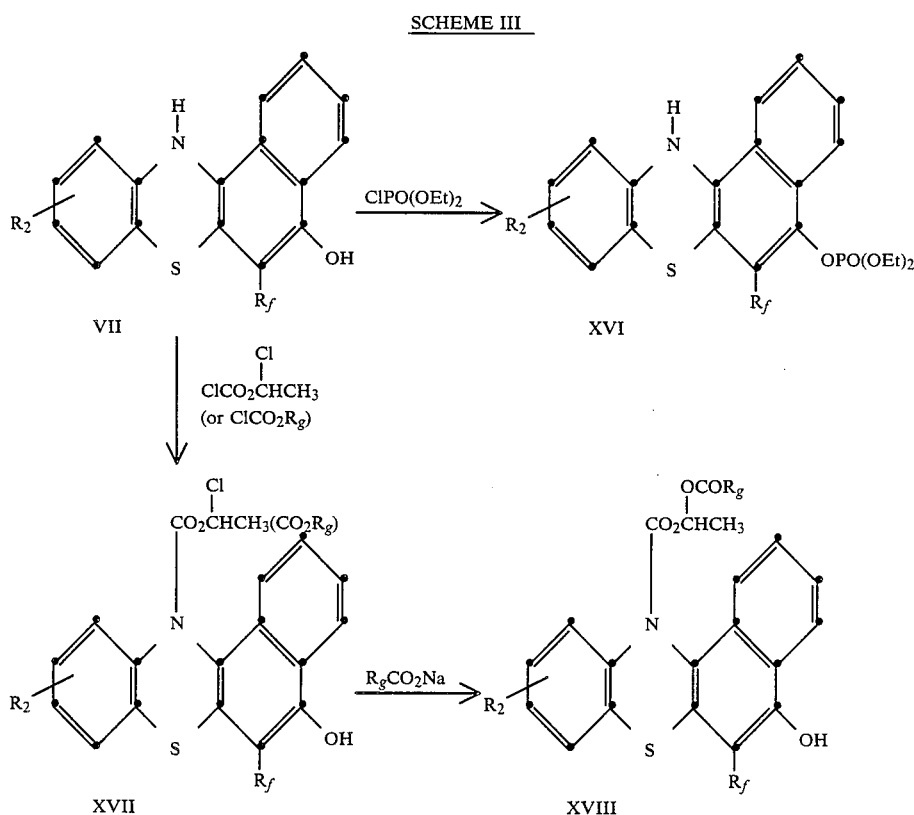

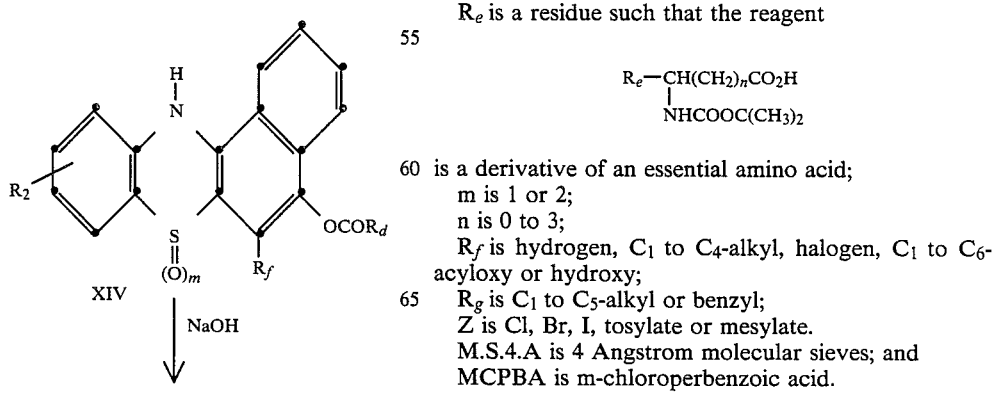

where:
$R_d$ is $C_1$ to $C_4$-alkyl or phenyl;
$R_e$ is a residue such that the reagent $$R_e-\underset{NHCOOC(CH_3)_2}{CH(CH_2)_nCO_2H}$$

is a derivative of an essential amino acid;
m is 1 or 2;
n is 0 to 3;
$R_f$ is hydrogen, $C_1$ to $C_4$-alkyl, halogen, $C_1$ to $C_6$-acyloxy or hydroxy;
$R_g$ is $C_1$ to $C_5$-alkyl or benzyl;
Z is Cl, Br, I, tosylate or mesylate.
M.S.4.A is 4 Angstrom molecular sieves; and
MCPBA is m-chloroperbenzoic acid.

SCHEME IV
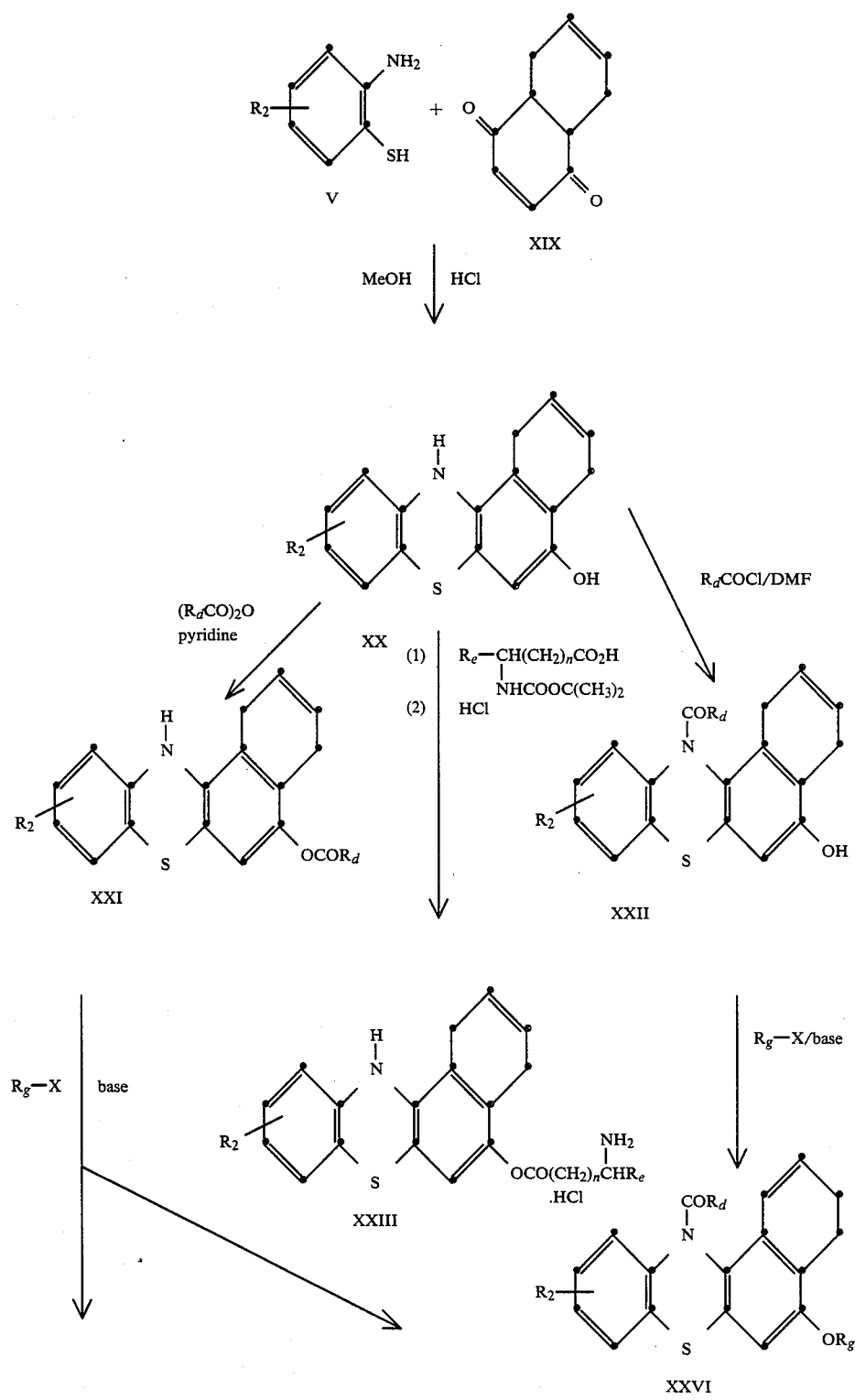

SCHEME IV -continued

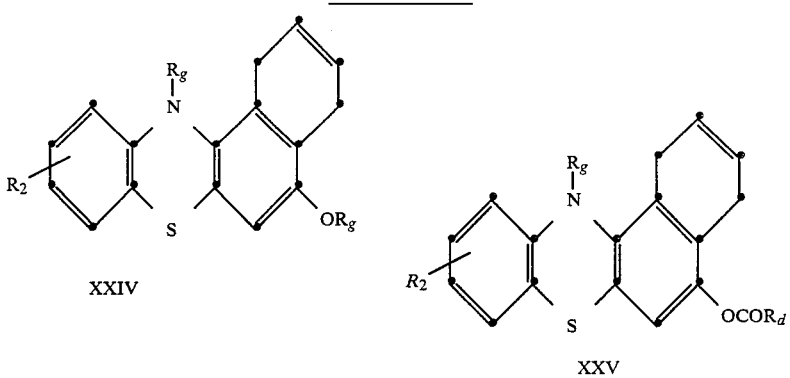

Reaction of a napthoquinone (IV), optimally two equivalents, with a 2-aminobenzenethiol (V), in a solvent such as acetic acid, acetic acid-water, or a lower alkanol at from −20° to +60° C. for 0.25 to 6 hours, yields the benzo[a]phenothiazin-5-one (VI). Preferably, the solvent is methanol or ethanol, at 0° to 25° C. for 0.5 to 2 hours. Reduction of VI to VII is carried out with a reducing agent, such as sodium hydrosulfite, in a suitable solvent system by stirring at from 10° to 50° C. (preferably at room temperature) for 1 to 12 hours (preferably 1 to 4 hours). The solvent system may be a homogeneous one, such as dimethylformamide-water or dichlormethane-water (Scheme I).

The O-acyl compounds (VIII) are prepared by reacting compound VII with the desired acid anhydride in pyridine at a temperature of from −25° to +75° C. (preferably at 0° to 50° C.) for from 1 hour to 24 hours (preferably 4 to 15 hours) (Scheme I).

The O-aminoacyl compounds (IX) are prepared from VIII by reacting the latter with an N-blocked amino acid and dicyclohexylcarbodiimide (DCC), followed by removal of the blocking group by treatment with HCl (Scheme I).

The N-acyl compound (X) may be prepared from VII by reacting the latter with an acyl halide, such as acetyl chloride, in a solvent, such as dimethyl formamide, at from 0° to 50° C. (preferably at room temperature) for from 0.5 to 4 hours, depending on the rate of reaction of the particular components (Scheme I).

To obtain the N,O-dialkyl compounds (XI), compound VIII is reacted with an alkyl halide or a methyl sulfonate (preferably an alkyl iodide) in the presence of a strong base, such as sodium hydride or potassium t-butoxide, in a solvent, such as tetrahydrofuran or dimethylformamide, at 0° to 60° C. (preferably room temperature) for from 1 to 24 hours (preferably for from 1 to 10 hours).

In this same reaction, some of the N-alkyl-O-acyl compound (XII) is also obtained, and is separated from compound XI by chromatography. The N-acyl-O-alkyl compounds (XIII) are prepared from compound X by a procedure similar to that used to prepare XI and XII (Scheme I).

The sulfoxide derivative (XIV) (m=1) are prepared by treating VIII with peracid such as peracetic acid or meta-chloroperbenzoic acid (MCPBA), in a solvent, such as methylene chloride or methylene chloride-methanol, for 0.5 to 4 hours at 0° to 30° C. The sulfones (XIV) (m=2) are obtained by reacting VIII with a peracid in methylene chloride-methanol, or preferably 1,2-dichloro-ethane-ethanol, at the reflux temperature of the mixture for from 12 to 24 hours, depending upon the rate of reaction. Hydrolysis of XIV to XV is carried out by reaction with a base (for example, LiOH, NaOH or KOH) in a mixed solvent, such as methanol-water or ethanol-water, at from 0° to 60° C. (preferably room temperature), for from 5 minutes to 180 minutes (preferably 10 minutes to 90 minutes) (Scheme II).

To prepare a carbamate derivative such as XVII, compound VII is reacted with the appropriate chloroformate reagent in a suitable solvent, such as tetrahydrofuran, dioxane or preferably acetonitrile, and the mixture heated to reflux for 4 to 24 hours. Reaction of the appropriate chloroalkylcarbamate (XVII) with a metal salt of a carboxylic acid then yields the acyloxyalkoxycarbonyl compound (XVIII). Preferred salts are those of silver, mercury (II) or sodium, using the corresponding free acid as a solvent, and heating the reaction mixture at 0° to 100° C., for from 10 minutes to 2 hours (Scheme III).

The 1,4-dihydro series of compounds (XX) is prepared by condensing a 2-amino benzenethiol (V) with diketone (XIX) under conditions similar to those used for the reaction between IV and V. Preparation of compounds XXI to XXVI is carried out by methodology very similar to that described in Scheme I to obtain compounds VIII to XIII (Scheme IV).

Some of the benzo[a]-phenothiazin-5-one derivatives used as starting materials are described in our co-pending applications U.S. Ser. No. 591,134, filed Mar. 19, 1984 and European patent application 115,394. The disclosure of these applications is hereby incorporated herein by reference.

It will be evident to one skilled in the art that $R_2$ must be chosen so as to be compatible with the reaction outlined in Schemes I to IV.

Certain of the compounds of the present invention contain one or more centers of asymmetry. This invention is meant to include both the racemic and the resolved forms of such compounds. In addition, certain compounds of the present invention can exist as atropisomers. All such atropisomers represented by the two-dimensional representation of the structures are also meant to be included in the present invention.

An x-ray crystallographic analysis of a representative compound of Formula I, 5-hydroxy-12-(1-acetoxyethoxycarbonyl)-12H-benzo[a]phenothiazine (XVIII; $R_2=R_f=H$, $R_g=Me$) indicates the following 3-dimensional structure

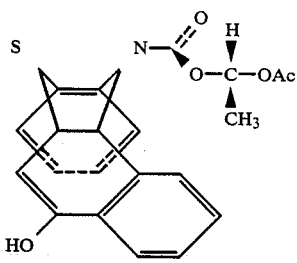

CONFORMER 1 OF 5-HYDROXY-N-(1-ACETOXYETHOXY-CARBONYL)-12H—BENZO-[a]PHENOTHIAZINE

This compound exists as one isomer with the stereochemistry cis between the acetoxyethoxy group of the side-chain and the benzene ring A of the tetracyclic ring system. As shown, the asymmetric side-chain carbon center has the S configuration, however the mirror image of the indicated structure is also present in the crystal.

A 250 MHz proton NMR spectrum of this compound, dissolved in dimethylformamide-d7 (LDMF-d7), kept for one hour at room temperature, then cooled to −50° C. to record the spectrum, shows a multiplicity of peaks in excess of what would be expected from such a structure. In particular, the methyl group of the acetyl unit appears as four sharp singlets, of approximately equal intensity, at 1.89, 1.91, 1.99 and 2.28 parts per million (ppm).

In another experiment, a sample of the crystalline compound was dissolved in DMF-d7, pre-cooled to −50° C., and the NMR spectrum taken quickly at −50° C. The resulting spectrum showed only two peaks for the acetyl methyl protons at 1.91 and 1.99 ppm. As the sample was warmed, these two signals coalesced to a singlet at about 30° C. (1.91 ppm); at about 80° C., a second singlet appeared (2.04 ppm), and at 170° C., these two singlets began to coalesce.

In another NMR study of the compound, five samples were dissolved in DMF-d7 at 25° C., and then stored at −78° C., after being held for 0, 5, 15, 30 and 60 minutes at 25° C. The NMR spectra of these samples at −50° C. showed that the two previously described peaks at 1.91 and 1.99 ppm were present initially, but that over time, the two additional peaks at 1.89 and 2.28 ppm gradually appeared, until after 60 minutes, all four peaks were present in approximately equal amounts.

As a result of the x-ray and NMR studies, it is concluded that there is a single conformational isomer of compound XVIII present in the crystalline form, and that this isomer equilibrated upon dissolution at room temperature, over a period of approximtely one hour, to a mixture of at least four observable conformational isomers, which may possibly be represented as follows:

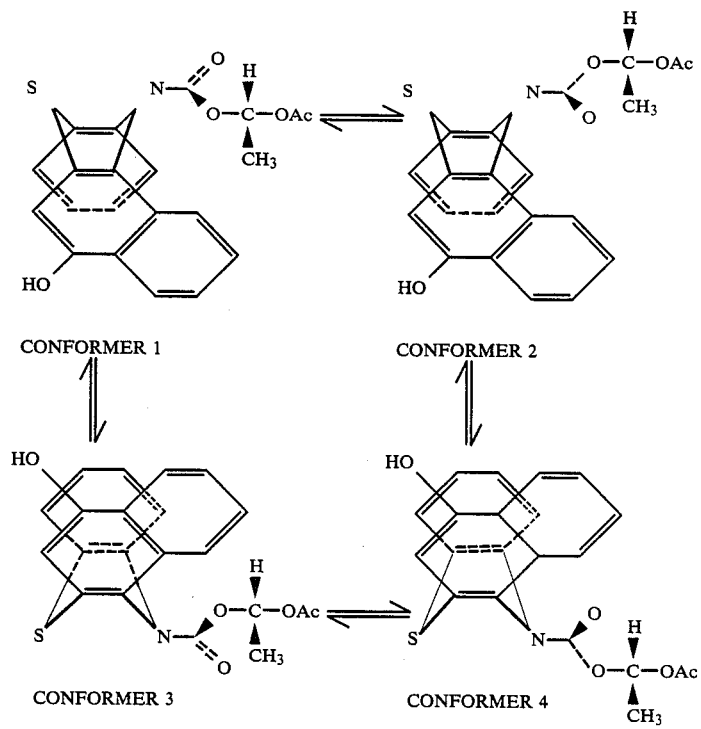

CONFORMATIONS OF 5-HYDROXY-N—(1-ACETOXYETHOXYCARBONYL)-12H—BENZO-[a]PHENOTHIAZINE

A solid form of the compound containing all four conformational isomers may be obtained by rapid precipitation of the compound from solution with water. Suitable solvents from which to precipitate the compound include water-miscible protic and aprotic solvents, such as DMF, ethanol, acetone, dimethylsulfoxide (DMSO), polyethylene glycol-200 (PEG-200), PEG-400, acetic acid, 1,2-propanediol, and the like. The melting point of the solid thus obtained is somewhat variable because of its amorphous nature, but it is always lower than the melting point of the crystalline compound (195°–196° C.), in agreement with the presence of a mixture of isomers. Another suitable method for obtaining the compound in an amorphous form is by lyophilization from a suitable solvent, such as acetic acid, p-butanol, benzene, cyclohexane, carbon tetrachloride, chloroform, dioxane, and the like.

The compounds of Formula I have unexpected activity as inhibitors of the mammalian biosynthesis of both leukotriene $B_4$, as well as leukotrienes $C_4$, $D_4$, $E_4$ and $F_4$, the active elements of slow-reacting substance of anaphylaxis (SRS-A). This inhibition of the biosynthesis of leukotrienes indicates that the compositions would be useful to treat, prevent or ameliorate, in mammals and especially in humans (1) pulmonary conditions, including diseases, such as asthma, (2) allergies and allergic reactions, such as allergic rhinitis, contact dermatitis, allergic conjunctivitis and the like, (3) inflammation, such as arthritis, (4) pain, (5) skin conditions, such as psoriasis and the like and (5) cardiovascular conditions, such as angina and the like.

Representative compounds of Formula I have been tested using one or more of the following assays to determine their mammalian leukotriene biosynthesis-inhibiting activity or their activity in assays relevant to the above disease conditions.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/ml. A 500 μl aliquot of PMN suspension and test compound are preincubated for 2 minutes at 37° C., followed by the addition of 10 μM A-23187. The suspension is stirred for an additional 4 minutes then bioassayed for $LTB_4$ content by adding an aliquot to a second 500 μl portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ration of transmission change in the sample to the transmission change in the compound-free control.

Asthmatic Rat Assay

Rats were obtained from an inbred line of asthmatic rats. Both female and male rats from 200 to 300 g were used.

Egg albumin (EA), grade V, crystallized and lyophilized, was obtained from Sigma Chemical Co., St. Louis. *Bordetella pertussis* vaccine, containing $30 \times 10^9$ killed bacteria per ml was obtained from the Institut Armand-Frappier, Laval des Rapides, Quebec. Aluminum hydroxide was obtained from the Regis Chemical Company, Chicago.

The challenge and subsequent respiratory recordings were carried out in a clear plastic box with internal dimensions 10×6×4 inches. The top of the box was removable; in use, it was held firmly in place by four clamps and an airtight seal was maintained by a soft rubber gasket. Through the center of each end of the chamber a Devilbiss nebulizer (No. 40) was inserted via an airtight seal and each end of the box also had an outlet. A Fleisch No. 0000 pneumotachograph was inserted into one end of the box and coupled to a Grass volumetric pressure transducer (PT5-A) which was then connected to a Beckman Type R Dynograph through appropriate couplers. While aerosolizing the antigen, the outlets were open and the pneumotachograph was isolated from the chamber. The outlets were closed and the pneumotachograph and the chamber were connected during the recording or the respiratory patterns. For challenge, 2 ml of a 3% solution of antigen in saline was placed into each nebulizer and the aerosol was generated with air from a small Potter diaphragm pump operating at 10 psi and a flow of 8 liters/minute.

Rats were sensitized by injecting (s.c.) 1 ml of a suspension containing 1 mg EA and 200 mg aluminum hydroxide in saline. Simultaneously, they received an injection (i.p.) of 0.5 ml of *B. pertussis* vaccine. They were used between days 14 and 18 postsensitization. In order to eliminate the serotonin component of the response, rats were pretreated intravenously 5 minutes prior to aerosol challenge with 30 gm $kg^{-1}$ methysergide. Rats were then exposed to an aerosol of 3% EA in saline for exactly 1 minute, then their respiratory profiles were recorded for a further 25–30 minutes. The duration of continuous dyspnoea was measured from the respiratory recordings.

Compounds were generally administered either intraperitoneally 1 hour prior to challenge or orally 1½ hours prior to challenge. They were either dissolved in dimethylsulfoxide or suspended in 0.1% methocel and 0.5% Tween 80. The volume injected was 2 ml $kg^{-1}$ (intraperitoneally) or 10 ml $kg^{-1}$ (orally). Prior to oral treatment rats were starved overnight. Their activity was determined in terms of their ability to decrease the duration of symptoms of dyspnoea in comparison with a group of vehicle-treated controls. Usually, a compound was evaluated at a series of doses and an $ED_{50}$ was determined. This was defined as the dose (mg/kg) which would inhibit the duration of symptoms by 50%.

PAF-Induced Hyperalgesia Assay

Female Sprague-Dawley rats, 35–40 g were fasted overnight. Platelet activating factor, PAF, (L-lecithin B-acetyl O-alkyl) 1 μg/0.1 ml was given by subplantar injection in the rat paw. The compounds to be evaluated were homogenized in Aqueous Vehicle (0.9% benzyl alcohol, 0.5% Tween 80 and 0.4% methyl-cellulose) and administered orally in a volume of 0.1 ml, 30 minutes prior to PAF.

Animals were tested 1, 2, 3 and 4 hours after PAF administration. The vocalization threshold, defined as the pressure (mmHg) needed to evoke a squeak response, was recorded for both the injected and contralateral paw. No animal was subjected to pressure greater than 60 mmHg. Hyperalgesia is defined as a decrease in vocalization threshold as compared to a normal paw. Percent inhibition of hyperalgesia was calculated as the proportion of animals with vocalization thresholds greater than 200% of controls.

Following in Table III is data obtained using these various assays with representative compounds of Formula I.

TABLE III
ASSAY RESULTS

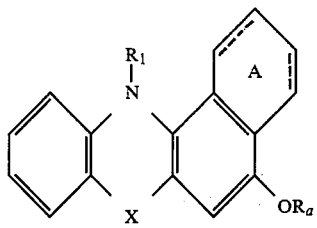

| Ring A | $R_1$ | $R_a$ | X | PMN $IC_{50}$ (mg/ml) | Asth. Rat % Inhibition and Dose (mg/kg) (p.o.) | PAF Induced Hyperalgesia % Inhibition and Dose (mg/kg) (p.o.) |
|---|---|---|---|---|---|---|
| aromatic | H | Ac | S | 0.025–0.05 | $ED_{50}$: 4 mg/kg | $ED_{50}$: 0.145 mg/kg |
| aromatic | Me | Me | S | 5 | — | 80% (3) |
|          |    |    |   |   |   | 40% (1) |
| aromatic | Me | Ac | S | 0.05 | — | 30–60% (1) |
| aromatic | Ac | H | S | 1–5 | — | — |
| aromatic | Ac | Me | S | 5 | — | — |
| aromatic | H | H | S | 0.02–0.1 | 54% (1.5) | — |
| aromatic | H | $COCH_2NH_2 \cdot HCl$ | S | 0.04–0.2 | 44% (3) | — |
|          |   |   |   |   |   | 21% (1.5) |
| 1,4-dihydro | H | H | S | 0.04 | — | — |
| aromatic | H | $CH_2OCH_3$ | S | 1–5 | — | — |
| aromatic | H | COPh | S | 0.5 | 18% (5) | — |
| aromatic | H | $COC(CH_3)_3$ | S | 0.1–1 | 54% (5) | — |
| aromatic | H | $OR_a=H$ | S | 0.2–1 | — | — |
| aromatic | H | Me | S | 0.1 | — | — |
| aromatic | H | $PO(OEt)_2$ | S | 0.2–1 | — | — |
| aromatic | Ac | Ac | S | — | 47% (5) | — |
| aromatic | $CO_2\underset{\underset{OAc}{|}}{C}HCH_3$ | H | S | 0.2–1 | 49% (1.5) | 60% (3) |
| aromatic | H | H | $SO_2$ | 0.2–1 | 67% (5) | — |
| aromatic | H | Ac | $SO_2$ | 0.2–1 | 42% (5) | — |
| aromatic | H | Ac | SO | 0.2–1 | — | — |
| aromatic | H | Ac | O | 0.05–0.5 | 44% (5) | — |

In certain biological tests, the amorphous mixture of four isomers shows advantageous biological activity over the crystalline material. Representative results comparing the two forms of the compound are shown in the accompanying Table IV (where doses are in mg/kg, p.o.).

TABLE IV
Asthmatic Rat Assay Results on Compound XVIII
($R_2 = R_f = H$, $R_g = Me$)

| Solid Form | Vehicle | Dose | % Inhibition | |
|---|---|---|---|---|
| Crystalline (1 Conformer) | 0.4% Tween 80/ 0.5% Methocel | 5 | 81 | $ED_{50} = 1.5$ |
|  |  | 2 | 61 |  |
|  |  | 1.5 | 49 |  |
|  |  | 0.5 | 19 |  |
|  | 1% Methocel | 2 | 28 |  |
| Amorphous (4 Conformers) | 0.4% Tween 80/ 0.5% Methocel | 2 | 57 | $ED_{50} = 1.0$ |
|  |  | 1.5 | 52 |  |
|  |  | 0.5 | 48 |  |
|  | 1% Methocel | 1.5 | 59 | $ED_{50} = 1.0$ |
|  |  | 0.5 | 36 |  |

The pharmaceutical compositions will contain a sufficient amount of one or more of the compounds of Formula I in a dosage form suitable for inhibiting the mammalian biosynthesis of leukotrienes or, for the treatment desired. The effective concentration of Formula I compound in the composition will vary as required by the severity of the condition to be treated, the particular compound of Formula I, the mode of administration, dosage form and pharmacological effect and level desired. A general daily dosage of Formula I (for uses other than cytoprotection) will range from about 100 micrograms to 200 mg/kg of body weight. A preferred daily dosage range is from 1 mg/kg to 100 mg/kg and a most preferred dosage range is from 2 mg/kg to 50 mg/kg.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 micrograms to about 200 micrograms, administered as needed.

For treating allergies or allergic reactions, such as allergic conjunctivitis, allergic rhinitis and the like, the Formula I compound may be administered by any conventional mode, e.g. orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight of the active ingredient (Formula I compound) may vary from about 0.001 to about 10%.

For treating inflammation, the mode of administration may be oral, parenteral, by suppository and the like. The various dosage forms are the same as those described above.

For treating skin diseases, such as psoriasis, atopic dermatitis and the like, oral, topical or parenteral administration is useful. For topical application to the diseased area, salves, patches, controlled release patches, emulsions, etc., are convenient dosage forms.

For use as an analgesic, i.e., for treating pain, any suitable mode of administration may be used, e.g., oral, parenteral, by insufflation, by suppository and the like.

For treating cardiovascular conditions, such as angina pectoris, etc., any suitable mode of administration, e.g., oral, parenteral, topical, insufflation, etc., and dosage form, e.g., pills, liquid formulations, controlled release capsules, controlled release skin patches, etc., may be used.

In addition to the common dosage forms set out above, the compound of Formula I may also be administered for the various utilities and indications or for inhibiting leukotriene synthesis by controlled release means and/or delivery devices, such as those described in U.S. No. 3,845,770; U.S. No. 3,916,899; U.S. No. 3,536,809; U.S. No. 3,598,123; U.S. No. 3,630,200 and U.S. No. 4,008,719. Dosage forms for application to treat the eye are also disclosed in U.S. No. 4,348,398.

In preparing suitable dosage forms, conventional compounding procedures and ingredients, e.g., diluents, carriers, etc. may be used.

Two assays may be used to measure cyto-protective ability. These assays are; (A) an ethanol-induced gastric ulcer assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen minutes prior to ethanol administration, groups of rats each receive either an aqueous vehicle, (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

As cytoprotective agents, the compounds of Formula I may generally be administered at a dosage range of 0.02 mg/kg to 100 mg/kg of body weight. The exact amount of inhibitor to be used will depend on, inter alia, whether it is being administered to heal damaged cells or to avoid future damage, on the nature of the damaged cells (e.g., gastro-intestinal ulcerations vs. nephrotic necrosis), and on the nature of the cuasative agent. An example of the use of a compound of Formula I in avoiding future damage would be co-administration of a compound of the formula I with a non-steroidal antiinflammatory drug that might otherwise cause such damage (for example, indomethacin). For such use, the compound of Formula I is administered from 30 minutes prior to, up to 30 minutes after administration of the NSAID. Preferably, it is administered prior to or simultaneously with the NSAID (for example, in a combination dosage form).

The effective daily dosage level for compounds of Formulae I inducing cytoprotection in mammals, especially humans, will range from about 0.02 mg/kg to about 100 mg/kg, preferably from about 0.02 mg/kg to about 30 mg/kg. The dosage may be administered in single or divided individual doses, using various dosage forms, as described above.

The pharmaceutical compositions of the present invention comprise a compound of formula I as an active ingredient or a pharmaceutically-acceptable salt thereof, and may also contain a pharmaceutically-acceptable carrier and optionally other therapeutic ingredients. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene inhibitors of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations, such as, for example, powders, capsules and tablets. Because of their ease of administration, tablets and capsules represent the most advantageous oral dosage unit form, in which case, solid pharmaceutical carriers are obviously employed. If desired, tablets may be sugar-coated or enteric-coated by standard techniques.

In addition to the common dosage forms set out above, the compounds of Formula I may also be administered by controlled-release means and/or delivery devices, such as those described in U.S. Pat. Nos. 3,845,770; 3,916,899; 3,536,809; 3,598,123; 3,630,200; and 4,008,719, the disclosure of which is incorporated herein, by reference.

Pharmaceutical compositions of the present invention suitable for oral administration and by inhalation in the case of asthma therapy may be presented as discrete units, such as capsules, cachets or tablets, each containing a predetermined amount of the active ingredient, as a powder or granules or as a solution or a suspension in an aqueous liquid, a non-aqueous liquid, an oil-in-water emulsion or a water-in-oil emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of Formula I:

| Injectable Suspension | mg/ml |
|---|---|
| Compound of Formula I | 2.0 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Tablet | mg/tablet |
|---|---|
| Compound of Formula I | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

In addition to the compounds of Formula I, the pharmaceutical compositions of the present invention may also contain other active ingredients, such as cyclooxygenase inhibitors, non-steroidal anti-inflammatory drugs (NSAIDs), peripheral analgesic agents, such as zomepirac diflunisal and the like. The weight ratio of the compound of the Formula I to the second active ingredient may be varied, and will depend upon the effective dose of each ingredient. Generally, an effective dose of each will be used, except in those cases where a beneficial synergism may be realized. Thus, for example, when a compound of the Formula I is combined with an NSAID the weight ratio of the compound of the Formula I to the NSAID will generally range from about 1000:1 to about 1:1000, preferably from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically-acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally-related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally may be in the form of a pharmaceutically-acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally-related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH$_2$COOH group (which optionally may be in the form of a pharmaceutically-acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally-related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

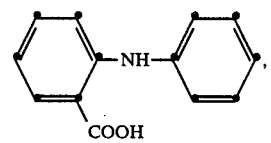

which may bear a variety of substituents and in which the free —COOH group may be in the form of a pharmaceutically-acceptable salt group, e.g., —COO$^-$Na$^+$.

The biphenylcarboxylic acid derivatives which may be used comprise: diflunisal and flufenisal. Structurally-related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

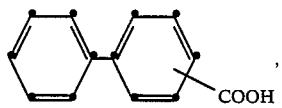

which may bear a variety of substituents and in which the free —COOH group may be in the form of a pharmaceutically-acceptable salt group, e.g., —COO$^-$Na$^+$.

The oxicams which may be used in the present invention comprise: piroxicam, sudoxicam, isoxicam and 4-hydroxyl-1,2-benzothiazine, 1,1-dioxide 4-(N-phenyl)-carboxamide. Structurally-related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

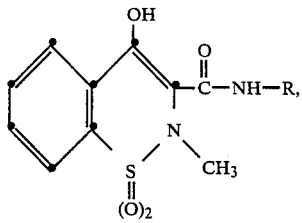

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITCl, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically-acceptable salts thereof.

Pharmaceutical compositions comprising the Formula I compounds may also contain other inhibitors of the biosynthesis of the leukotrienes, such as are disclosed in pending U.S. patent applications Ser. No. 539,342, filed Oct. 5, 1983; Ser. No. 459,924, filed Jan. 21, 1983; Ser. No. 539,215, filed Oct. 5, 1983; and Ser. No. 547,161, filed Oct. 31, 1983; which are incorporated herein by reference.

The compounds of the Formula I may also be used in combination with leukotriene-antagonists, such as those disclosed in copending applications U.S. Ser. Nos. 520,051 and 520,052, filed Aug. 5, 1983 which are hereby incorporated herein by reference and others known in the art such as those disclosed in European patent application Nos. 56,172 and 61,800; and in U.K. Patent Specification No. 2,058,785, which are hereby incorporated herein by reference.

Pharmaceutical compositions comprising the Formula I compounds may also contain, as the second active ingredient, antihistaminic agents, such as benadryl, dramamine, histadyl, phenergan and the like. Alternatively, they may include prostaglandin-antagonists such as those disclosed in European patent application 11,067· or thromboxane antagonists such as those disclosed in U.S. No. Pat. No. 4,237,160. They may also contain histidine decarboxyase-inhibitors such as α-fluoromethylhistidine, described in U.S. Pat. No. 4,325,961. The compounds of the Formula I may also be advantageously combined with an H$_1$- or H$_2$-receptor antagonist, such as, for instance, cimetidine, ranitidine, terfenadine, famotidine, aminothiadiazoles disclosed in EP application No. 40,696 and like compounds, such as those disclosed in U.S. Pat. Nos. 4,283,408; 4,362,736; 4,394,508; European patent application No. 40,696 and a pending application, U.S.S.N. 301,616, filed Sept. 14, 1981. The pharmaceutical compositions may also contain a K$^+$/H$^+$ ATPase inhibitor, such as omeprazole, disclosed in U.S. Pat. No. 4,255,431, and the like. Each of the references referred to in this paragraph is hereby incorporated herein by reference.

The following examples are provided to aid in the interpretation of the claims appearing below. They are not intended as a limitation upon the scope of said claims. All temperatures are reported in degrees Celsius (°C.) and are uncorrected.

EXAMPLE 1

Preparation of 5-acetoxy-12H-benzo[a]phenothiazine

Acetic anhydride (2 ml) was added to a solution of 5-hydroxy-12H-benzo[a]phenothiazine (1) (1.4 gm) in pyridine (10 ml) and stirred for 15 minutes. The reaction mixture was concentrated under vacuum and ice-water was added to the residue. The resulting precipitate was filtered, air-dried and washed with ethyl acetate to afford the title compound.

m.p. 184°–5° Anal. $C_{18}H_{13}NO_2S$ Calcd.: C, 70.34; H, 4.26; N, 4.56; S, 10.43. Found: C, 70.28; H, 4.32; N, 4.53; S, 10.51. Ref. (1): C.A. 70: 69169z. S. African 6801,996.

EXAMPLE 2

Preparation of
5-methoxy-12-methyl-12H-benzo[a]phenothiazine and
5-acetoxy-12-methyl-12H-benzo[a]phenothiazine Potassium tert. butoxide (1.3 gm) was added to a solution of 5-acetoxy-12H-benzo[a]phenothiazine (from Example 1) (2.0 gm) and methyl iodide (4 ml) in DMF (20 ml). The reaction mixture was cooled with an ice-bath and stirred for 15 minutes. Diethyl ether (100 ml) was added to the reaction mixture followed by brine (100 ml). The ether layer was decanted, washed with brine, dried and evaporated to dryness. The resulting oily residue was chromatographed on silica gel (10% EtOAc/hexane) to afford 5-methoxy-12-methyl-12H-benzo[a]phenothiazine.

M.P. 123°–4°, Anal. $C_{18}H_{15}NOS$ Calcd.: C, 76.69; H, 5.15; N, 4.77; S, 10.93. Found: C, 73.64; H, 5.30; N, 4.71; S, 11.00 followed by 5-acetoxy-12-methyl-12H-benzo[a]phenothiazine.

m.p. 109°–110° Anal. $C_{19}H_{15}NO_2S$ Calcd.: C, 71.01; H, 4.70; N, 4.36; S, 9.98. Found: C, 71.25; H, 4.90; N, 4.26; S, 10.12.

EXAMPLE 3

Preparation of
12-acetyl-5-hydroxy-12H-benzo[a]phenothiazine

Acetyl chloride (2 ml) was added to a solution of 5-hydroxy-12H-benzo[a]phenothiazine (1) (2.65 gm) in DMF (10 ml) and stirred for 30 minutes. Diethyl ether (100 ml) was added to the reaction mixture followed by ice-water (50 ml). The aqueous layer was decanted and the organic layer containing a solid was evaporated to dryness. The resulting residue was treated with acetone and filtered to afford the title compound.

m.p. 230°. Anal. $C_{18}H_{13}NO_2S$. Calcd.: C, 70.34; H, 4.26; N, 4.56; S, 10.43. Found: C, 70.43; H, 4.38; N, 4.55; S, 10.62. Ref. (1): C.A. 70: 69169z. S. African 6801,966.

EXAMPLE 4

Preparation of
12-Acetyl-5-methoxy-12H-benzo[a]phenothiazine

Potassium tert-butoxide (800 mg) was added to a solution of 12-acetyl-5-hydroxy-12H-benzo[a]phenothiazine (950 mg) (from Example 3) and methyl iodide (1.5 ml) in DMF (10 ml) and stirred for 15 minutes. Water (80 ml) was added to the reaction mixture and the precipitate was filtered to afford the title compound.

m.p. 208°–9° Anal. $C_{19}H_{15}NO_2S$ Calcd.: C, 71.01; H, 4.70; N, 4.36; S, 9.98. Found: C, 70.97; H, 4.84; N, 4.30; S, 10.07.

EXAMPLE 5

Preparation of
5-aminoacetoxy-12H-benzo[a]phenothiazine-hydrochloride salt

Dicyclohexylcarbodiimide (21 g) was added to a solution of 5-hydroxy-12H-benzo[a]phenothiazine (4.2 g) and N-tert-butyloxycarbonyl glycine (8.4 g) in THF (150 ml) followed by the addition of DMAP (0.2 g). The reaction mixture was stirred for 15 minutes, filtered and the filtrate evaporated to dryness. The residue was dissolved in EtOAc, washed with a solution of NaHCO$_3$, dried and evaporated to dryness. The resulting oily residue was chromatographed on silica gel (5% EtOAc/CH$_2$Cl$_2$) to afford 5-tert-butyloxycarbonylamino acetoxy-12H-benzo[a]phenothiazine. m.p. 175° as an intermediate.

The above intermediate (1 g) was dissolved in CH$_2$Cl$_2$ (35 ml) cooled to 0° and HCl (gas) was bubbled into the solution for 15 minutes. The precipitate was filtered to afford the title compound.

m.p. 189° Anal. $C_{18}H_{13}N_2O_2S \cdot HCl$ Calcd.: C, 60.25; H, 4.21; N, 7.80; S, 8.93; Cl, 9.88. Found: C, 60.00; H, 4.30; N, 7.90; S, 8.78; Cl, 10.16.

EXAMPLE 6

Preparation of
5-Hydroxy-1,4-dihydro-12H-benzo[a]phenothiazine

A solution of 2-aminothiophenol (385 mg) in methanol (3 ml) was added to a solution of 4a, 5, 8, 8a-tetrahydro-1,4-naphtoquinone (Ref.: Ber. 62, 2361 (1929)) (500 mg) in methanol (10 ml) and stirred for 1 hour. Then conc. HCl (2 ml) was added and the mixture was stirred for another 2 hours. Ethyl acetate was added to the reaction mixture followed by a solution of NaHCO$_3$. The organic layer was decanted, dried and evaporated to dryness. The resulting oily residue was chromatographed on silica gel (CH$_2$Cl$_2$) to afford the title compound.

m.p. 166° Anal. $C_{16}H_{13}NOS$ Calcd.: C, 71.88; H, 4.90; N, 5.23; S, 11.99. Found: C, 71.74; H, 4.88; N, 5.25; S, 12.17.

EXAMPLE 7

Preparation of
5-Hydroxy-6-methyl-12H-benzo[a]phenothiazine and
5-acetoxy-6-methyl-12H-benzo[a]phenothiazine A solution of sodium hydrosulfite (40 g) in water (0.5 l) was added to a suspension of 6-methyl-5H-benzo[a]phenothiazine-5-one (10.4 g) in ethyl acetate (1 l) and stirred for 2 hours. The organic layer was decanted, dried and evaporated to dryness. The resulting residue was triturated with ether and filtered to afford 5-hydroxy-6-methyl-12H-benzo[a]phenothiazine as an air sensitive solid.

The above compound (3 gm) was dissolved in a mixture of pyridine (20 ml) and acetic anhydride (10 ml) and stirred for 15 minutes. The reaction mixture was concentrated under vacuum and the residue triturated with diethyl ether and filtered. A sample was chromatographed on silica gel (CH$_2$Cl$_2$) to afford the title compound, m.p. 170°, Anal. $C_{19}H_{15}NO_2S$ Calcd.: C, 71.00; H, 4.70; N, 4.35; S, 9.97. Found: C, 70.95; H, 4.80; N, 4.24; S, 10.14.

EXAMPLE 8

Preparation of
5-Benzoyloxy-12H-benzo[a]phenothiazine

Following the procedure of Example 1 but substituting benzoic anhydride for acetic anhydride, the title compound was obtained, m.p. 171° C. Anal. $C_{13}H_{15}NO_2S$; Calcd.: C, 74.78; H, 4.09; N, 3.79; S, 8.68. Found: C, 74.93; H, 4.22; N, 3.96; S, 8.57.

EXAMPLE 9

Preparation of 5-Trimethylacetoxy-12H-benzo[a]phenothiazine

Following the procedure of Example 1 but substituting trimethyl acetic anhydride for acetic anhydride, the title compound was obtained, m.p. 142° C. Anal. $C_{21}H_{19}NO_2S$; Calcd.: C, 72.18; H, 5.48; N, 4.01; S, 9.17. Found: C, 72.15; H, 5.46; N, 4.21; S, 9.34.

EXAMPLE 10

Preparation of 5-Methoxymethoxy-12H-benzo[a]phenothiazine

Sodium hydride (75 mg) was added to a solution of 5-hydroxy-12H-benzo[a]phenothiazine (1) (500 mg) and chloromethyl methyl ether (154 mg) in THF (10 ml) and the reaction mixture was stirred for 15 minutes. Diethyl ether (60 ml) was added to the reaction mixture followed by water (60 ml). The ether layer was decanted, dried and evaporated to dryness. The resulting residue was chromatographed on silica gel ($CH_2Cl_1$/hexane (7:3)) to afford the title compound, m.p. 103° C. Anal. $C_{18}H_{15}NO_2S$; Calcd.: C, 69.87; H, 4.89; N, 4.53; S, 10.36. Found: C, 69.75; H, 5.01; N, 4.41; S, 10.53.

EXAMPLE 11

Synthesis of 5-Acetoxy-12-acetyl-12H-benzo[a]phenothiazine

To a mixture of 5-acetoxy-12H-benzo[a]phenothiazine (3.0 g) and powdered 4 Angstrom molecular sieves (7.5 g) in 1,2-dichloroethane (75 ml) there was added slowly acetyl bromide (1.05 ml). The mixture was stirred at room temperature for 1 hour, then filtered. The filtrate was evaporated down to an oil which was triturated with a mixture of ether and hexane to afford solid title product (3 g), m.p. 141°–142° C.

EXAMPLE 12

Synthesis of 5-Methoxy-12H-benzo[a]phenothiazine

To a solution of 5-hydroxy-12H-benzo[a]phenothiazine (2.65 g) and methyl iodide (2.5 ml) in DMF (dimethylformamide) (10 ml) there was added powdered potassium carbonate (2.0 g). The mixture was stirred at room temperature and after 15 minutes, another addition of potassium carbonate (2.0 g) and methyl iodide (2.0 ml) was done. The mixture was stirred for a further 20 minutes, then it was diluted with ethyl acetate (100 ml and washed with water (60 ml) twice, dried and evaporated down. The residue was triturated with ether to afford solid crude product which was filtered (1.7 g). This crude product was chromatographed on a column of silica gel, eluting with dichloromethane to afford pure title compound (1.33 g), m.p. 168°–170° C.

EXAMPLE 13

Synthesis of Diethyl 12H-benzo[a]phenothiazin-5-yl phosphate

To a solution of 5-hydroxy-12H-benzo[a]phenothiazine (1.5 g) and diethyl chlorophosphate (2 ml) in DMF (20 ml) there was added a powdered mixture of potassium carbonate (2 g) and potassium iodide (2 g). The reaction mixture was stirred at room temperature. After 30 minutes, a further addition of potassium carbonate and potassium iodide (2 g each) was made and stirring was continued. Two hours later more carbonate (2 g) and diethyl chlorophosphate (2 ml) were added, and then three hours later a final addition of carbonate (2 g) was made. The mixture was stirred for 3 days then diluted with ethyl acetate (60 ml) and the insolubles filtered. The filtrate was washed with water, dried and evaporated down. This residue was crystallized from acetone, then chromatographed on a column of silica gel, eluting first with 1:1, then 3:1 mixtures of ethyl acetate and hexane to afford pure title compound (337 mg), m.p. 162°–163° C.

EXAMPLE 14

Synthesis of 5-hydroxy-12-(1-acetoxyethoxycarbonyl)-12H-benzo[a]phenothiazine

Step 1: Preparation of α-Chloroethyl chloroformate

To a mixture of ethyl chloroformate (108.5 g) and sulfuryl chloride (138 g), benzoyl peroxide (1 g) was added and it was refluxed for 20 hours. The reaction mixture was distilled and the liquid boiling above 110° was collected. This was then fractionated using a 30 cm column packed with glass helices to give 32 g of pure alpha-chloroethyl chloroformate, b.p. 118°–119°.

Step 2: Preparation of 5-hydroxy-12-(α-chloroethoxycarbonyl)-12H-benzo[a]phenothiazine A mixture of 5-hydroxy-12H-benzo[a]phenothiazine (5 g) and α-chloroethyl chloroformate (10 g) in tetrahydrofuran (20 ml) was refluxed for 9 hours, then the volatile components were evaporated away and the residue chromatographed on a column of silica gel, eluting with a 1:9 ethyl acetate-hexane mixture to afford the title compound (4 g) as an oil.

Step 3: Preparation of 5-hydroxy-12-(1-acetoxyethoxycarbonyl)-12H-benzo[a]phenothiazine The product from Step 2 (4 g) and sodium acetate (6 g) were refluxed together in glacial acetic acid (60 ml) for 1 hour. The mixture was cooled, diluted with ethyl acetate (300 ml) and washed with water (3×100 ml), then with aqueous sodium bicarbonate and again with water, dried and evaporated down. The residue was chromatographed on a column of silica gel eluting with a 1:9 mixture of ethyl acetate-hexane to afford, after trituration in ether and filtration, the pure title compound (1.2 g), m.p. 195°–196° C.

Step 4: Conversion of crystalline 5-hydroxy-12-(1-acetoxyethoxycarbonyl)-12H-benzo[a]phenothiazine into an amorphous solid of 4 conformers The crystalline material obtained in Step 3 (20 g) was dissolved in acetone (500 ml) and the solution evaporated to an oily residue. Residual acetone was removed by co-evaporation with absolute ethanol (50 ml), twice. The residual thick oil was dissolved in absolute ethanol (about 25 ml) and the mixture stirred vigorously during the rapid addition of water (1 L). The gummy precipitate, on further stirring, became a solid. The mixture was allowed to settle, the milky supernatant decanted and the solid stirred in water (600 ml) until a fine solid was obtained. It was filtered and dried, to afford 17 g of amorphous 5-hydroxy-12-(1-acetoxyethoxycarbonyl)-12H-benzo[a]phenothiazine, m.p. 102°–112° C.

EXAMPLE 15

Synthesis of
5-acetoxy-9-methoxy-12H-benzo[a]phenothiazine

By following the procedures described in preparative Example 7, but substituting 9-methoxy-5H-benzo[a]phenothiazine-5-one for the 6-methyl analog as starting material, the title compound was obtained, m.p. 156°–158° C.

EXAMPLE 16

Synthesis of
5-Acetoxy-9-methyl-12H-benzo[a]phenothiazine

By following the procedures described in preparative Example 7, but substituting 9-methyl-5H-benzo[a]phenothiazine-5-one for the 6-methyl analog as starting material, the title compound was prepared, m.p. 193°–195° C.

EXAMPLE 17

Synthesis of
5-Acetoxy-9-fluoro-12H-benzo[a]phenothiazine

By following the procedures described in preparative Example 7, but substituting 9-fluoro-5H-benzo[a]phenothiazine-5-one for the 6-methyl analog as starting material, the title compound was obtained, m.p. 196°–198° C. (dec).

EXAMPLE 18

Synthesis of 5-Acetoxy-12H-benzo[a]phenoxazine

Applying the procedures described in preparative Example 7, but substituting 5H-benzo[a]phenoxazine-5-one for 6-methyl-5H-benzo[a]phenothiazine-5-one, the title compound was synthesized, m.p. 152°–155° C.

EXAMPLE 19

Synthesis of 5,6-Diacetoxy-12H-benzo[a]phenothiazine

By following the procedures described in preparative Example 7, but substituting 6-acetoxy-5H-benzo[a]phenothiazine-5-one for the 6-methyl analog as starting material there was obtained the title compound, m.p. 206°–207° C.

EXAMPLE 20

Synthesis of
12-Acetyl-5,6-diacetoxy-12H-benzo[a]phenothiazine

By following the procedure described in preparative Example 11, but substituting 5,6-diacetoxy-12H-benzo[a]phenothiazine for the 5-acetoxy analog as starting material, the title compound was obtained, m.p. 213°–214° C.

EXAMPLE 21

Synthesis of
12-Acetyl-5,6-dihydroxy-12H-benzo[a]phenothiazine

To a suspension of 12-acetyl-5,6-diacetoxy-12H-benzo[a]phenothiazine (450 mg) in acetone (10 ml) there was added 2N aqueous sodium hydroxide solution (10 ml) and the resulting mixture was stirred at room temperature for 45 minutes. It was then made slightly acidic by the addition of 10% aqueous acetic acid solution and the insolubles filtered and washed with water. The solid was swished in ethyl acetate to afford pure title compound (100 mg), m.p. 258°–260° C.

EXAMPLE 22

Synthesis of
5-Acetoxy-12H-benzo[a]phenothiazine-7-oxide

To a suspension of 5-acetoxy-12H-benzo[a]phenothiazine (10 g) in dichloromethane (125 cc) there was raidly added a solution of 85% m-chloroperoxybenzoic acid (6.61 g) in methanol (125 ml). At first the solids dissolved, then after a few minutes a new solid separated out of solution. After 1 and ½ hours the mixture was filtered and the solid washed with dichloromethane. The title compound was thus obtained pure (8.76 g), m.p. 179°–181° C.

EXAMPLE 23

Synthesis of
5-Acetoxy-12H-benzo[a]phenothiazine-7,7-dioxide

To a suspension of 5-acetoxy-12H-benzo[a]phenothiazine (10 g) in dichloromethane (125 ml) there was rapidly added a solution of 85% m-chloroperoxybenzoic acid (18 g) in methanol (125 ml). A solution resulted which rapidly began to deposit the sulfoxide. The mixture was heated to a gentle reflux and slowly the solid redissolved, then the sulfone began to crystallize out of solution. After 2 and ½ hours the mixture was allowed to cool down and it was filtered to afford nearly pure title product. A 1 gram sample was crystallized from THF (tetrahydrofuran) to afford pure product (504 mg), m.p. 284°–287° C.

EXAMPLE 24

Synthesis of
5-Hydroxy-12H-benzo[a]phenothiazine-7,7-dioxide

To a suspension of 5-acetoxy-12H-benzo[a]phenothiazine-7,7-dioxide (6.6 g) in methanol (200 ml) there was added 2N aqueous sodium hydroxide solution (132 ml) and the mixture was stirred in the absence of air at room temperature for 7 minutes; at that point an amber solution had resulted. There was rapidly added 10% aqueous acetic acid solution (200 ml) causing precipitation of the title compound which was collected by filtration (5.68 g). A sample (500 mg) was crystallized from THF affording purified product (250 mg), m.p. 334° C. (dec).

EXAMPLE 25

Synthesis of
5,6-Dihydroxy-12H-benzo[a]phenothiazine-7,7-dioxide

To a suspension of 6-hydroxy-5H-benzo[a]phenothiazine-5-one-7,7-dioxide (430 mg) in water (10 cc) and ethyl acetate (10 ml) there was added sodium dithionite (1 g). The suspension was stirred vigorously at room temperature for 2 hours, then the insolubles were filtered and washed with water and ethyl acetate. There was obtained 346 mg of the title compound, m.p. 330° C.

EXAMPLE 26

Synthesis of
5-Acetoxy-12-(1-acetoxyethoxycarbonyl)-12H-benzo[a]phenothiazine

By following the procedure of Example 1, but substituting the product of Example 14 for 5-hydroxy-12H-benzo[a]phenothiazine, the title compound was obtained, m.p. 76°–78°.

EXAMPLE 27

Synthesis of 5-Hydroxy-12-(12H-benzo[a]phenoxazine

By following the procedure of Example 14, Steps 2 and 3, but substituting 5-hydroxy-12H-benzo[a]phenoxazine for 5-hydroxy-12H-benzo[a]phenothiazine, the title compound is obtained.

EXAMPLE 28

Preparation of 5-hydroxy-12-(1-pivaloyloxyethoxycarbonyl)-12H-benzo[a]phenothiazine Following the procedure of Example 14, Step 3, but substituting sodium pivaloate for sodium acetate, and pivaloic acid for acetic acid, the title compound is obtained.

EXAMPLE 29

Preparation of 5-hydroxy-12-ethoxycarbonyl-12H-benzo[a]phenothiazine

Following the procedure of Example 14, Step 2, but substituting ethyl chloroformate for α-chloroethylchloroformate, the title compound was obtained, m.p. 205°–206° C.

EXAMPLE 30

Preparation of 5-hydroxy-12-isopropyloxycarbonyl-12H-benzo[a]phenothiazine

Following the procedure of Example 14, Step 2, but substituting isopropylchloroformate for α-chloroethylchloroformate, the title compound was obtained, m.p. 205°–206° C.

EXAMPLE 31

To a stirring solution of 500 g (2.34 mol) of 3H-phenothiaz-3-one in 12.5 L of glacia acetic acid was added 1.25 kg of ptassium dichromate. The mixture was stirred at room temperature for ½ hour. To this resulting mixture was then added 2.34 mol of a 1M solution of chlorine in glacial acetic acid dropwise over a period of 4 hours. The progress of the reaction was monitored by tlc to ensure no excess chlorine was added. After addition of chlorine was completed the mixture was stirred at room temperature for another ½ hour and was then poured into 120 L of $H_2O$ with vigorous stirring. The 4-chlorophenothiazin-3-one precipitated was allowed to settle overnight. The majority of the aqueous solution was siphoned and discarded and the rest was filtered. The filtered precipitate was washed thoroughly with water and then rinsed with methanol and was allowed to dry to give 504 g crude 4-chlorophenothiazin-3-one which was recrystallized from toluene.

EXAMPLE 32

4-((3-(4-Acetyl-3-hydroxy-2-propylphenoxy)-2-hydroxypropyl)thio)-gamma-oxobenzenebutanoic acid

A. Preparation of 4-methoxy-gamma-oxobenzenebutanoic Acid

Anisole (70.0 g) and succinic anhydride (65.0 g) were dissolved in 1,2-dichloroethane (1 liter) and the mixture was cooled to 0° C. To the resulting suspension there was added, in portions, $AlCl_3$ (172 g) and the resulting mixture was stirred with a mechanical stirrer for 1 hour. The mixture was then poured into a mixture of ice and water (about 1 liter) containing 50 ml of concentrated HCl. The resulting white solid was collected by filtration, washed with water and air-dried to yield 4-methoxy-gamma-oxobenzenebutanoic acid, mp 145°–147° C.

B. Preparation of 4-hydroxy)-gamma-oxobenzenebutanoic acid, methyl ester

A mixture of the compound from Step A (77.3 g), 48% HBr (310 ml), and acetic acid (620 ml) was heated under reflux for 18 hours. The resulting mixture was cooled to room temperature and poured into 3 liters of water. The resulting solution was extracted with ethyl acetate (3×500 ml). The combined organic layers were washed with water (4×200 ml), dried over $Na_2SO_4$, the solvents were removed by evaporation and the residue was dissolved in 10% HCl/methanol (500 ml). After 1 hour at room temperature the volatile components were removed by evaporation in vacuo. The resulting residue was triturated with hexane to yield the title compound, mp 115°–116°.

C. Preparation of 4-dimethylthiocarbamoyloxy-gamma-oxobenzenebutanoic acid, methyl ester A solution of the product from Step B, 25 g, in anhydrous dimethylformamide (DMF) (300 ml) was cooled to 0° and 99% NaH, 3.46 g, was added in two portions. The mixture was stirred for 1 hour at 0° then dimethylthiocarbamoyl chloride, 19.3 g, was added and the mixture heated at 90° under a $N_2$ atmosphere for 1.5 hours. The mixture was cooled to room temperature and diluted with water to 1,200 mL. The resulting solution was then extracted with ethyl acetate (3×500 ml). The combined organic layers were washed with brine and then dried over $Na_2SO_4$ and evaporated to dryness in vacuo to yield a residue which was purified by chromatography on silica gel to yield the title compound, mp 62°–64°.

D. Preparation of 4-dimethylcarbamoylthio-gamma-oxobenzenebutanoic acid, methyl ester The compound from Step C, 29.6 g, was heated at 200° for 10 hours under an $N_2$ atmosphere. The mixture was cooled to room temperature, dissolved in methylene chloride and purified by chromatography on silica gel to provide the title compound, mp 98°–100°.

E. Preparation of 4-mercapto-gamma-oxobenzene-butanoic acid, methyl ester

Sodium 280 mg, was dissolved in anhydrous methanol, 50 ml, under an $N_2$ atmosphere. To the resulting solution there was added 5.0 g of the compound from Step D. The mixture was stirred at room temperature overnight, then poured into a mixture containing 30 ml of water and 7 ml of concentrated HCl. The resulting yellow solid was collected by filtration, washed with water and dried in air to give the title compound, mp 83°–84°.

F. Preparation of 4-((3-(4-acetyl-3-hydroxy-2-propylphenoxy)-2-hydroxypropyl)thio)-gamma-oxobenzenebutanoic acid 2-Hydroxy-3-propyl-4-(2,3-epoxypropoxy)acetophenone (0.6 g, 2.4 mmole) was refluxed in 15 ml of methylethyl ketone with the product from step E (0.6 g, 2.4 mmole) for two days in the presence of 1.0 equivalent of $K_2CO_3$. The product was purified by chromatography on silica gel. The product, 0.9 g was saponified with KOH (1.5 equivalents) in a 25 ml mixture of methanol and water (10:1). The volatile components were removed under vacuum. The residue was taken up in water and acidified with citric acid. The aqueous phase was extracted twice with ethyl acetate, the organic layer was washed with brine, dried ($Na_2SO_4$) and evaporated to dryness to leave the acid residue which was triturated in hexane and filtered.

Analysis, Calculated: C, 62.18; H, 6.74. Observed: C, 62.14, H, 6.32.

EXAMPLE 33

4-((3-(4-Acetyl-3-hydroxy-2-propylphenoxy)propyl)-thio)-gamma-oxobenzenebutanoic acid Following the procedure of Step F of Example 32 but substituting an equivalent amount of 2-hydroxy-3-propyl-4-(3-bromopropyloxy)acetophenone for 2-hydroxy-3-propyl-4-(2,3-epoxypropoxy)-acetophenone, the title compound was obtained.

Analysis, calculated: C, 64.98; H, 6.14; S, 7.23. Observed: C, 65.09; H, 6.09; S, 7.28.

EXAMPLE 34

4-((3-(4-Acetyl-3-hydroxy-2-propylphenoxy)propyl)-thio)-3-fluoro-gamma-oxobenzenebutanoic acid Following the procedure of Example 32 but substituting an equivalent amount of 2-fluoroanisole for anisole in Step A and substituting an equivalent amount of 2-hydroxy-3-propyl-4-(3-bromopropoxy)acetophenone for 2-hydroxy-3-propyl-4-(2,3-epoxypropoxy)acetophenone in Step F, the title compound was obtained, m.p. 115°–116° C.

EXAMPLE 35

4-((3-(4-Acetyl-3-hydroxy-2-propylphenoxy)propyl)-thio)-2-fluoro-gamma-oxobenzenebutanoic acid Following the procedure of Example 34 but substituting 3-fluoroanisole for 2-fluoroanisole, the title compound was obtained, mp 149°–150° C.

EXAMPLE 36

4-(3-(4-Acetyl-3-hydroxy-2-propylphenoxy)propylsulfonyl)-2-fluoro-gamma-oxobenzenebutanoic acid The ester prepared according to the procedure of Example 35 dissolved in 50 mL $CH_2Cl_2$ was treated at room temperature with 2.5 equivalents of m-chloroperbenzoic acid for 2 hours. The reaction mixture was purified by chromatography on silica gel to yield the methyl ester of the title compound, that then was saponified by stirring with NaOh in methanol to yield the title compound, m.p. 116°–118°.

EXAMPLE 37

4-(3-(4-Acetyl-3-hydroxy-2-propylphenoxy)propylsulfonyl)-gamma-oxobenzenebutanoic acid The ester prepared according to the procedure of Example 33 was treated as in Example 36 to give, after saponification, the title compound, Analysis, calculated: C, 60.48; H, 5.92; S, 6.72. Observed: C, 60.51; H, 5.90; S, 6.48.

Claims to the invention follow.

What is claimed is:

1. A pharmaceutical composition for inhibiting leukotriene biosynthesis or action in mammals, which is a tablet, elixir, emulsion, injectable solution, capsule, aerosol spray, controlled release patch, thixotropic formulation, powder, suppository, cachet, or injectable suspension, containing a pharmaceutically-acceptable carrier and an effective amount of a compound having the formula (I):

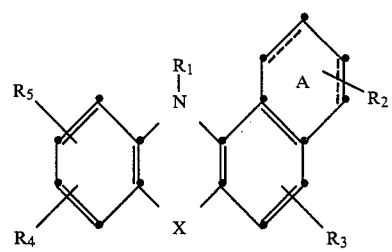

wherein:

X is O, S, SO or $SO_2$;

$R_1$ is H; $C_1$ to $C_6$-alkyl; $C_1$ to $C_6$-acyl; $C_1$ to $C_6$-aminoacyl; $C_1$ to $C_6$-acyloxy-$C_1$ to $C_6$-alkyl; $C_1$ to $C_6$-alkoxy-$C_1$ to $C_6$-alkyl;

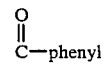

or

wherein the substituents of substituted phenyl are as defined below among the definitions of $R_{15}$; carbamoyl;

$SO_2$—$C_6H_4$-p—$CH_3$; $SO_2CH_3$; or $R_1$ is an acyl group, such that $R_1$—OH is an essential amino acid;

$R_2$, $R_3$, $R_4$ and $R_5$, all of which may be positioned anywhere on the structure, are independently selected from:

(1) hydrogen;
(2) alkyl having 1 to 6 carbon atoms;
(3) alkenyl having 2 to 6 carbon atoms;
(4) —$(CH_2)_n$M, wherein n is 0 to 6 and M is
 (a) $OR_{15}$, where $R_{15}$ is as defined below;
 (b) F, Cl, Br or I;
 (c) $CF_3$;

(d) SR$_{15}$ where R$_{15}$ is H; C$_1$ to C$_6$-alkoxy-C$_1$ to C$_6$-alkyl; C$_1$ to C$_6$-acyloxy-C$_1$ to C$_6$-alkyl; C$_1$ to C$_6$-alkyl; benzyl; —(CH$_2$)$_n$COOR$_6$, wherein n is 0 to 6; CN; formyl; C$_1$ to C$_4$-perfluoroalkyl; CH$_2$—R$_{12}$, wherein R$_{12}$ is C$_1$ to C$_5$-alkyldimethylamino or phenyl; phenyl; substituted phenyl, wherein the substituents are C$_1$ to C$_3$-alkyl, Cl, F, Br, I, CN, CF$_3$, COOR$_6$, CH$_2$COOR$_6$, (CH$_2$)$_p$NR$_8$R$_9$ where p is 0 to 2, C$_1$ to C$_3$-alkoxy or OH;

(e) phenyl or substituted phenyl, wherein substituted phenyl is as defined in the definition of R$_{15}$;

(f) COOR$_6$;

(g)

(h) tetrazole;

(i)
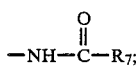

(j) —NR$_8$R$_9$;

(k) —NHSO$_2$R$_{10}$ wherein R$_{10}$ is OH, C$_1$ to C$_6$-alkyl, C$_1$ to C$_6$-alkoxy, or phenyl;

(l)
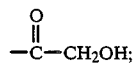

(m) —SOR$_{11}$ wherein R$_{11}$ is C$_1$ to C$_6$-alkyl; phenyl; substituted phenyl, where substituted phenyl is as defined in the definition of R$_{15}$; (CH$_2$)$_m$COOR$_6$ wherein m is 1 to 6; CN; formyl or perfluoro-C$_1$ to C$_4$-alkyl;

(n) —CONR$_8$R$_9$;

(o) —SO$_2$NR$_8$R$_9$;

(p) —SO2R$_{13}$, wherein R$_{13}$ is OH; C$_1$ to C$_6$-alkyl; H; phenyl; substituted phenyl, wherein substituted phenyl is as defined in the definition of R$_{15}$; (CH$_2$)$_m$COOR$_6$ wherein m is 1 to 6; CN; formyl or perfluoro-C$_1$ to C$_4$-alkyl;

(q) NO$_2$;

(r)
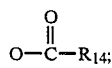

(s)
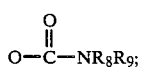

(t) —CN;

(u) —OPO(OR$_6$)$_2$; or (v) —OR$_a$, wherein R$_a$ is H; C$_1$ to C$_5$-alkyl; C$_1$ to C$_5$-acyl; C$_1$ to C$_6$-alkoxy-C$_1$ to C$_6$-alkyl; C$_1$ to C$_6$-acyloxy-C$_1$ to C$_6$-alkyl; C$_1$ to C$_4$-aminoacyl; carbamoyl;

or

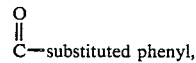

wherein substituted phenyl is as defined in the definition of R$_{15}$;

where R$_c$ is C$_1$ to C$_4$-alkyl;

where R$_d$ is C$_1$ to C$_4$-alkyl or C$_1$ to C$_6$-acyloxy-C$_1$ to C$_6$-alkyl; or is a structure such that —OR$_a$ is an ester of an essential amino acid; and (5) —(CHR$_6$)$_q$COOR$_6$, where q is 0 to 4; where each R$_6$ is independently H, phenyl or C$_1$ to C$_6$-alkyl; each R$_7$ is C$_1$ to C$_6$-alkyl, benzyl, phenyl or C$_1$ to C$_6$-acyloxy-C$_1$ to C$_6$-alkyl; each R$_8$ and each R$_9$ is independently H, phenyl or substituted phenyl, where substituted phenyl is as defined in the definition of R$_{15}$, or C$_1$ to C$_4$-alkyl; each R$_{14}$ is independently H, (CH$_2$)$_q$COOR$_6$ wherein q is 0 to 4, C$_1$ to C$_6$-alkyl, C$_1$ to C$_6$-alkoxy, C$_1$ to C$_6$-acyloxy-C$_1$ to C$_6$-alkoxy, phenyl or substituted phenyl wherein substituted phenyl is as defined in the definition of R$_{15}$, C$_1$ to C$_6$-aminoalkyl, or R$_{14}$ is such that R$_{14}$CO$_2$H is an essential amino acid; and ⫶ represents single or double bonds; and pharmaceutically-acceptable salts thereof.

2. The composition of claim 1 wherein the compounds are selected from compounds of the formula:

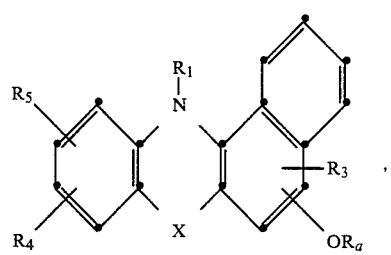

wherein:

R$_1$ is hydrogen, C$_1$ to C$_4$-alkyl, C$_1$ to C$_4$-acyl, C$_1$ to C$_6$-amino-acyl, C$_1$ to C$_6$-acyloxy-C$_1$ to C$_6$-alkyl, —COOR$_d$;

R$_3$, R$_4$ and R$_5$, all of which may be positioned anywhere on the structure, are each independently selected from hydrogen, halogen, CH$_3$, CF$_3$, COCH$_3$, R$_b$, SR$_6$, CH$_2$OH, OR$_b$, COOR$_b$ and CH$_2$COOR$_b$, where each R$_b$ is independently selected from H and C$_1$ to C$_4$-alkyl; and X, $R_a$, $R_d$ and $R_6$ are as defined in claim 1, and $OR_a$ may be positioned anywhere on the structure.

3. The composition of claim 2, wherein the compounds are selected from compounds of the Formula:

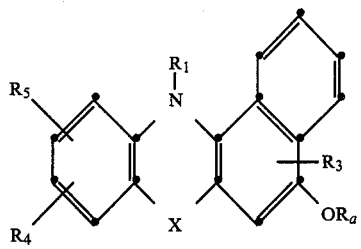

(III)

wherein X is O or S, and $R_1$, $R_3$, $R_4$, $R_5$ and $R_a$ are as defined in claim 2, and $R_3$, $R_4$ and $R_5$ may be positioned anywhere in the structure.

4. The composition of claim 3, wherein X is S and $R_1$, $R_3$, $R_4$, $R_5$ and $R_a$ are as defined in claim 3, and $R_3$, $R_4$ and $R_5$ may be positioned anywhere in the structure, with the proviso that at least one of $R_1$ or $R_a$ is other than hydrogen.

5. The composition of claim 1 wherein the compound is a compound of the formula:

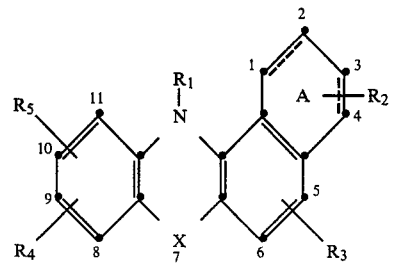

(I)

having one of the following substituent patterns:

| X | Ring A | $R_1$ | $R_2$ | $R_3$ | $R_4$ | $R_5$ |
|---|---|---|---|---|---|---|
| S | aromatic | H | 5-OH | H | H | H |
| S | aromatic | H | 5-OCOCH$_3$ | 6-Cl | H | H |
| S | aromatic | H | H | H | H | H |
| S | aromatic | H | 5-OH | 6-Cl | H | H |
| S | aromatic | H | 5-OH | 6-Cl | 9-Cl | H |
| S | aromatic | H | 5-OH | 6-Cl | 9-OCH$_3$ | H |
| S | aromatic | H | 5-OCOCH$_3$ | 6-Cl | 9-CH$_3$ | H |
| O | aromatic | H | 5-OH | H | H | H |
| O | aromatic | H | 5-OCOCH$_3$ | H | H | H |
| SO | aromatic | H | 5-OH | H | H | H |
| SO$_2$ | aromatic | H | 5-OH | H | H | H |
| SO | aromatic | H | H | H | H | H |
| SO$_2$ | aromatic | H | H | H | H | H |
| SO | aromatic | COCH$_3$ | H | H | H | H |
| S | aromatic | H | 1-CO$_2$H | H | H | H |
| S | aromatic | CH$_3$ | 2-Et | H | H | H |
| S | aromatic | COCH$_3$ | 2-COCH$_3$ | H | H | H |
| S | aromatic | H | 2-COCH$_3$ | H | H | H |
| S | aromatic | H | H | H | H | 10-phenyl |
| S | aromatic | H | H | H | 8-CH$_3$ | 11-CH$_3$ |
| S | aromatic | H | H | H | H | 10-COCH$_3$ |
| S | aromatic | H | 5-OH | 6-NHCOCH$_3$ | 9-F | H |
| S | aromatic | H | 5-OH | 6-NH—phenyl | 9-Cl | H |
| SO | aromatic | H | 5-OAc | 6-Cl | H | 10-CF$_3$ |
| SO | aromatic | H | 5-OCH$_2$Ph | 6-Cl | H | 10-CF$_3$ |
| S | aromatic | H | 5-OH | 6-Cl | 9-CH$_3$ | 11-CH$_3$ |
| S | aromatic | H | 5-OCH$_3$ | 6-Cl | 9-OCH$_3$ | H |
| SO$_2$ | 1,4-dihydro | H | 5-OH | H | H | H |
| SO$_2$ | aromatic | COCH$_3$ | 4-CH$_3$ | H | 9-SCH$_3$ | H |
| O | aromatic | H | H | H | 9-SO$_2$CF$_3$ | H |
| O | aromatic | H | H | H | 11-CH$_3$ | H |
| S | aromatic | COCH$_3$ | 5-OCOMe | H | H | H |
| S | aromatic | CH$_2$OAc | 5-OH | H | H | H |
| S | aromatic | CH$_2$OAc | 5-OCOMe | H | H | H |
| S | aromatic | Me | 5-OH | H | H | H |
| S | aromatic | H | 5-OCOCH$_3$ | H | H | H |
| S | aromatic | CH$_3$ | 5-OCH$_3$ | H | H | H |
| S | aromatic | CH$_3$ | 5-OCOCH$_3$ | H | H | H |
| S | aromatic | COCH$_3$ | 5-OH | H | H | H |
| S | aromatic | COCH$_3$ | 5-OCH$_3$ | H | H | H |
| S | aromatic | H | 5-OCOCH$_2$NH$_2$ | H | H | H |
| S | 1,4-dihydro | H | 5-OH | H | H | H |
| S | aromatic | H | 5-OCOCH(CH$_3$)$_2$ | H | H | H |
| S | aromatic | H | 5-OCOC(CH$_3$)$_3$ | H | H | H |
| S | aromatic | H | 5-OCOC$_6$H$_5$ | H | H | H |
| S | aromatic | H | 5-OH | 6-CH$_3$ | H | H |
| S | aromatic | H | 5-OCOCH$_3$ | 6-CH$_3$ | H | H |
| S | aromatic | H | 5-OH | 1-OH | 6-CH$_3$ | H |
| S | aromatic | H | 5-OCOCH$_3$ | 1-OH | 6-CH$_3$ | H |
| S | aromatic | H | 5-OH | 1-OCH$_3$ | 6-CH$_3$ | H |
| S | aromatic | H | 5-OCOCH$_3$ | 1-OCH$_3$ | 6-CH$_3$ | H |
| S | aromatic | H | 5-OCOC(CH$_3$)$_3$ | 1-OCH$_3$ | 6-CH$_3$ | H |
| S | 1,4-dihydro | H | 5-OCOCH$_3$ | H | H | H |
| SO$_2$ | aromatic | H | 5-OCOCH$_3$ | H | H | H |
| SO | aromatic | H | 5-OCOCH$_3$ | H | H | H |

-continued

| X | Ring A | R$_1$ | R$_2$ | R$_3$ | R$_4$ | R$_5$ |
|---|---|---|---|---|---|---|
| SO$_2$ | aromatic | H | 5-OCOCH$_3$ | H | H | H |
| S | aromatic | H | 5-OCH$_2$OCH$_3$ | H | H | H |
| S | aromatic | H | 5-OCH$_3$ | H | H | H |
| S | aromatic | H | 5-OCOC$_6$H$_4$—p-OMe | H | H | H |
| S | aromatic | H | 5-OCOC$_6$H$_4$—p-Cl | H | H | H |
| S | aromatic | H | 5-OCOC$_6$H$_4$—p-NH$_2$ | H | H | H |
| S | aromatic | H | 5-OCOC$_6$H$_4$—p-CO$_2$H | H | H | H |
| S | aromatic | H | 5-OCOC$_6$H$_4$—O—CF$_3$ | H | H | H |
| S | aromatic | H | 5-OCOC$_6$H$_4$—m-CN | H | H | H |
| S | aromatic | H | 5-OCO(CH$_2$)$_2$CO$_2$H | H | H | H |
| S | aromatic | H | 5-OCO(CH$_2$)$_4$CO$_2$H | H | H | H |
| S | aromatic | H | 5-OCOCH(NH$_2$)CH$_3$ | H | H | H |
| S | aromatic | H | 5-OCOCH(NH$_2$)CH$_2$C$_6$H$_5$ | H | H | H |
| S | aromatic | CO$_2$CHCH$_3$ \| OAc | 5-OH | H | H | H |
| S | aromatic | CO$_2$CHCH$_3$ \| OAc | 5-OAc | H | H | H |
| S | aromatic | CO$_2$CHCH$_3$ \| OAc | 5-OCO$_2$CHCH$_3$ \| OAc | H | H | H |
| S | aromatic | H | 5-OCO$_2$CHCH$_3$ \| OAc | H | H | H |
| S | aromatic | H | 5-OPO(OEt)$_2$ | H | H | H |
| S | aromatic | H | 5-OH | 9-OMe | H | H |
| S | aromatic | H | 5-OAc | 9-OMe | H | H |
| S | aromatic | H | 5-OH | 9-Me | H | H |
| S | aromatic | H | 5-OAc | 9-Me | H | H |
| S | aromatic | H | 5-OH | 9-F | H | H |
| S | aromatic | H | 5-OAc | 9-F | H | H |
| S | aromatic | H | 5-OH | 6-OAc | H | H |
| S | aromatic | H | 5-OAc | 6-OAc | H | H |
| S | aromatic | Ac | 5-OH | 6-OH | H | H |
| S | aromatic | Ac | 5-OAc | 6-OAc | H | H |
| SO$_2$ | aromatic | H | 5-OH | 6-OH | H | H |
| O | aromatic | OAc \| CO$_2$CHCH$_3$ | 5-OH | H | H | H |
| SO$_2$ | aromatic | OAc \| CO$_2$CHCH$_3$ | 5-OH | H | H | H |
| S | aromatic | OCOC(CH$_3$)$_3$ \| CO$_2$CHCH$_3$ | 5-OH | H | H | H |
| S | aromatic | CO$_2$C$_2$H$_5$ | 5-OH | H | H | H |
| S | aromatic | CO$_2$CH(CH$_3$)$_2$ | 5-OH | H | H | H |
| S | aromatic | OAc \| CHCH$_3$ | 5-OH | H | H | H |
| S | aromatic | OCOC(CH$_3$)$_3$ \| CHCH$_3$ | 5-OH | H | H | H |
| S | aromatic | OAc \| CO$_2$CHCH$_3$ | 5-OH | 6-Cl | H | H |
| S | aromatic | OAc \| CO$_2$CHCH$_3$ | 5-OH | 6-CF$_3$ | H | H |
| S | aromatic | OAc \| CO$_2$CHCH$_3$ | 5-OH | 6-F | H | H |

6. The composition of claim 1 wherein X is O.
7. The composition of claim 1 wherein X is S.
8. The composition of claim 1 wherein X is SO.
9. The composition of claim 1 wherein X is SO$_2$.
10. The composition of claim 1 containing an effective amount of one or more additional active ingredients selected from the group consisting of piroxicam, aspirin, 4-chlorophenothiazin-3-one, 4-(3-(4-acetyl-3-hydroxy-2-propylphenoxy)-propylsulfonyl-gamma-oxo-benzene butanoic acid, benadryl, 3-hydroxymethyldibenzo[b,f]-thiepin-5,5-dioxide, α-fluoromethylhistidine, indomethacin, and famotidine.

11. A pharmaceutical composition of claim 10, wherein said additional active ingredient is indomethacin.

12. A pharmaceutical composition of claim 10, wherein the weight ratio of the compound of claim 1 to said additional active ingredient ranges from about 1000:1 to about 1:1000.

13. A composition of claim 11, wherein said ratio ranges from about 200:1 to about 1:200.

14. A method of inhibiting mammalian leukotriene biosynthesis or action which comprises administering to a mammal in need of rrelief, an effective amount of a composition of claim 1.

* * * * *